US011890292B2

(12) United States Patent
Nezami

(10) Patent No.: US 11,890,292 B2
(45) Date of Patent: Feb. 6, 2024

(54) COMPOSITIONS, METHODS, SYSTEMS AND/OR KITS FOR PREVENTING AND/OR TREATING NEOPLASMS

(71) Applicant: Research Cancer Institute of America, Fresno, CA (US)

(72) Inventor: Mohammed Amin Nezami, Clovis, CA (US)

(73) Assignee: Research Cancer Institute of America, Newport Beach, CA (US)

( * ) Notice: Subject to any disclaimer, the term of this patent is extended or adjusted under 35 U.S.C. 154(b) by 523 days.

(21) Appl. No.: 16/488,565

(22) PCT Filed: Feb. 26, 2018

(86) PCT No.: PCT/US2018/019767
§ 371 (c)(1),
(2) Date: Aug. 23, 2019

(87) PCT Pub. No.: WO2018/157081
PCT Pub. Date: Aug. 30, 2018

(65) Prior Publication Data
US 2021/0283149 A1    Sep. 16, 2021

Related U.S. Application Data

(60) Provisional application No. 62/464,296, filed on Feb. 27, 2017.

(51) Int. Cl.
*A61K 31/675* (2006.01)
*A61P 35/00* (2006.01)
*A61K 9/00* (2006.01)
*A61K 31/192* (2006.01)
*A61K 31/353* (2006.01)

(52) U.S. Cl.
CPC .......... *A61K 31/675* (2013.01); *A61K 9/0019* (2013.01); *A61K 31/192* (2013.01); *A61K 31/353* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 4,569,836 | A | 2/1986 | Gordon |
| 6,299,925 | B1 | 10/2001 | Xiong et al. |
| 6,376,525 | B1 | 4/2002 | Kong |
| 8,933,078 | B2 | 1/2015 | Nezami |
| 9,364,500 | B2 | 6/2016 | Nezami |
| 9,439,899 | B2 | 9/2016 | Proia |
| 10,016,392 | B2 | 6/2018 | Nezami |
| 2003/0103954 | A1 | 6/2003 | Rosenbloom |
| 2003/0105031 | A1 | 6/2003 | Rosenbloom |
| 2006/0035981 | A1 | 2/2006 | Mazzio et al. |
| 2006/0057230 | A1 | 3/2006 | Chow |
| 2007/0190022 | A1 | 8/2007 | Bacopoulos et al. |
| 2007/0190114 | A1 | 8/2007 | Smart |
| 2008/0305096 | A1 | 12/2008 | Verdegem et al. |
| 2010/0239596 | A1 | 9/2010 | Lee et al. |
| 2010/0316733 | A1 | 12/2010 | Locklear |
| 2010/0330087 | A1 | 12/2010 | Newell et al. |
| 2011/0104100 | A1 | 5/2011 | Riordan et al. |
| 2011/0118309 | A1 | 5/2011 | Atadja |
| 2011/0224290 | A1 | 9/2011 | Estrela Ariquel et al. |
| 2012/0121730 | A1 | 5/2012 | Singh |
| 2012/0269861 | A1 | 10/2012 | Sherman et al. |
| 2013/0011488 | A1 | 1/2013 | Nezami |
| 2013/0014753 | A1 | 1/2013 | Nezami |
| 2013/0129809 | A1 | 5/2013 | Srivastava et al. |
| 2015/0366838 | A1 | 12/2015 | Lines |
| 2017/0014376 | A1 | 1/2017 | Nezami |
| 2017/0020842 | A1 | 1/2017 | Elmann |
| 2017/0224654 | A1 | 8/2017 | Armstrong et al. |
| 2017/0285027 | A1 | 10/2017 | Fantl |
| 2018/0133278 | A1 | 5/2018 | Atamaniuk et al. |
| 2019/0125791 | A1 | 5/2019 | Wilmotte |
| 2019/0167634 | A1 | 6/2019 | Nezami |
| 2020/0147030 | A1 | 5/2020 | Nezami |
| 2020/0206183 | A1 | 7/2020 | Nezami |
| 2021/0015787 | A1 | 1/2021 | Nezami |
| 2021/0401799 | A1 | 12/2021 | Nexami |
| 2022/0087946 | A1 | 3/2022 | Nezami |
| 2023/0072294 | A1 | 3/2023 | Nezami |

FOREIGN PATENT DOCUMENTS

| | | |
|---|---|---|
| CN | 1537161 | 10/2004 |
| EP | 1 847 274 | 10/2007 |
| JP | 05-070348 | 3/1993 |

(Continued)

OTHER PUBLICATIONS

Cheng et al., Aug. 31, 1989, The study of green tea extract's anti-tumor effect and mechanism of TPA, Zhonggu Kuangzhan Institute of Technology, 11(4):259-264.
Xu et al., Mar. 16, 2015, Enhancing the anti-colon cancer activity of quercetin by self-assembled micelles, International Journal of Nanomedicine, 10:2051-2063.
Zhang, Nov. 15, 2009, Inhibition of glycolysis to the biologic characteristics of pancreatic cancer cell PANC-1 and it mechanism, Kyangyao Health Science and Technology Appraisal, p. 10.
American Cancer Society, 2019, How chemotherapy drugs work, https://www.cancer.org/content/dam/CRC/PDF/Public/8418.00.pdf, 9 pp.
Patnaik et al., Jun. 2019, Drugs targeting epigenetic modifications and plausible therapeutic strategies against colorectal cancer, Frontiers in Pharmacology, 10(588). 15 pp.

(Continued)

*Primary Examiner* — Brian J Davis
(74) *Attorney, Agent, or Firm* — Knobbe, Martens, Olson & Bear, LLP

(57) ABSTRACT

Provided herein are compositions, methods, systems and/or kits for preventing and/or treating neoplasms using at least one modulator selected from quercetin, sodium phenyl butyrate and epigallocatechin-3-gallate in combination with one or more anti-cancer agents. The compositions, methods, systems and/or kits are used to prevent and/or treat neoplasms that are resistant to the one or more anti-cancer agents when administered alone.

15 Claims, 3 Drawing Sheets

(56) References Cited

FOREIGN PATENT DOCUMENTS

| | | |
|---|---|---|
| JP | 2006 298781 | 11/2006 |
| WO | WO 97/47317 | 12/1997 |
| WO | WO 05/023179 | 3/2005 |
| WO | WO 05/083123 | 9/2005 |
| WO | WO 06/059237 | 6/2006 |
| WO | WO 07/121088 | 10/2007 |
| WO | WO 08/011363 | 1/2008 |
| WO | WO 08/082856 | 7/2008 |
| WO | WO 09/019721 | 2/2009 |
| WO | WO 11/112156 | 9/2011 |
| WO | WO 14/091078 | 6/2014 |
| WO | WO 14/111268 | 7/2014 |
| WO | WO 16/054237 | 4/2016 |
| WO | WO 18/170457 | 9/2018 |

OTHER PUBLICATIONS

Taylor, 2017, Synergism of quercetin and sodium butyrate for controlling growth of glioblastoma, Master's thesis, University of South Carolina, retrieved from https://scholarcommons.sc.edu.etd. 4149, 102 pp.

Xintaropoulou et al., 2008, A comparative analysis of inhibitors of the glycolysis pathway in breast and ovarian cancer cell line models, Oncotarget, 6(27):25677-25695.

Akbas et al, "The effect of quercetin on topotecan cytotoxicity in MCF-7 and MDA-MB 231 human breast cancer cells." J Surg Res. May 1, 2005;125(1):49-55.

Alleva et al., 2005, α-Lipoic acid supplementation inhibits oxidative damage, accelerating chronic wound healing in patients undergoing hyperbaric oxygen therapy, Biochemical and Biophysical Research Communications, 333:404-410.

Amirkhosravi et al., "Pentoxifylline inhibits hypoxia-induced upregulation of tumor cell tissue factor and vascular endothelial growth factor." ThrombHaemost. Oct. 1998;80(4):598-602.

Arce et al., 2006, A proof-of-principle study of epigenetic therapy added to neoadjuvant doxorubiin cyclophosphamide for locally advanced breast cancer, PLoS ONE, 2006, 1(1):e98.

Armeanu et al., "Natural killer cell-mediated lysis of hepatoma cells via specific induction of NKG2D ligands by the histone deacetylase inhibitor sodium valproate" Can Res Jul. 15, 2005 vol. 65 No. 14 pp. 6321-6329.

Bai et al., Jan. 2010, Myricetin and quercetin are naturally-occuring co-substrates of cyclooxygenases in vivo, Prostaglandins Leukot Essent Fatty Acids, 82(1):1-11.

Baker et al., "A practical assay of lipoate in biologic fluids and liver in health and disease." Free Radic Biol Med. Sep. 1998; 25(4-5):473-479.

Befon et al., "Continuous Subcutaneous Octreotide in Gastrointestinal Cancer Patients: Pain Control and B-Endorphin Levels", Anticancer Research, 20:4039-4046 (2000) (abstract).

Bettuzzi et al., "Chemoprevention of human prostate cancer by oral administration of green tea catechins in volunteers with high-grade prostate intraepithelial neoplasia: a preliminary report from a one-year proof-of principle study," Cancer Res, Jan. 15, 2006, 66:1234-1240.

Bonnet et al., "A mitochondria-K+ channel axis is suppressed in cancer and its normalization promotes apoptosis and inhibits cancer growth." Cancer Cell. Jan. 2007;11(1):37-51.

Boyd, "Insulin and cancer." Integr Cancer Ther. Dec. 2003, 2(4):315-29.

Cai et al., "Restorative effect of quercetin on subcellular distribution of daunorubicin in multidrug resistant leukemia cell lines K562/ADM and HL-60/ADM." Department of Oncology, Shanghai No. 6 People's Hospital, Shanghai Jiaotong University, Shanghai 200233, P.R. China, Ai Zheng. Dec. 2004;23(12):1611-1615 (abstract).

Camacho et al., "Phase I dose escalation clinical trial of phenylbutyrate sodium administered twice daily to patients with advanced solid tumors." Invest New Drugs. Apr. 2007;25(2):131-8.

Carducci et al., "Phenylbutyrate induces apoptosis in human prostate cancer and is more potent than phenylacetate." Clin Cancer Res. Feb. 1996;2(2):379-87.

Castillo et al., "The effects of the bioflavonoid quercetin on squamous cell carcinoma of the head and neck origin." Am J Surg. 1989;158(4):351-5.

Chang et al., 2006, Reactive oxygen species production is involved in quercetin-induced apoptosis in human helatoma cells, Nutr Cancer, 55(2):201-209 (abstract).

Chen et al., "Quercetin and trichostatin a cooperatively kill human leukemia cells", Pharmazie 60:856-860 (2005).

Chen, L. et al., "Absorption, distribution, elimination of tea polyphenols in rats," Drug Metab Dispos, Sep. 1997, 25(9):1045-1050.

Choi et al., "Mechanism of alpha-lipoic acid-induced apoptosis of lung cancer cells." Ann N Y Acad Sci. Aug. 2009;1171:149-55.

Cruz-Correa et al., Aug. 2006, Combination treatment with curcumin and quercetin of adenomas in familial adenomatous polyposis, Clinical Gastroenterology and Hepatology, 4(8):1035-1038.

Dashwood et al., "Dietary histone deacetylase inhibitors: From cells to mice to man" Semin Cancer Biol. Oct. 2007, 17(5):363-369.

Dell'Antone, "Inactivation of H+-vacuolar ATPase by the energy blocker 3-bromopyruvate, a new antitumour agent" Life Sci. Oct. 19, 2006;79(21):2049-55.

Dreher et al., "Role of oxygen free radicals in cancer development." Eur J Cancer. Jan. 1996;32A(1):30-38.

Du et al., "Dietary quercetin combining intratumoral doxorubicin injection synergistically induces rejection of established breast cancer in mice." Int Immunopharmacol. Jul. 2010;10(7):819-26.

Du et al., "Quercetin greatly improved therapeutic index of doxorubicin against 4T1 breast cancer by its opposing effects on HIF-1.alpha. in tumor and normal cells." Cancer Chemother Pharmacol. Jan. 2010;65(2):277-87.

Farr, Charles, "The Therapeutic Use of Intravenous Hydrogen Peroxide", A Review, Experimental Evidence of Physiological Effect and Clinical Experience, Nov. 1986, 11 pp.

Ferry et al., "Phase I clinical trial of the flavonoid quercetin: pharmacokinetics and evidence for in vivo tyrosine kinase inhibition." Clin Cancer Res. Apr. 1996;2(4):659-68.

Ganapathy-Kanniappan et al., "3-Bromopyruvate induces endoplasmic reticulum stress, overcomes autophagy and causes apoptosis in human HCC cell lines." Anticancer Res. Mar. 2010;30(3):923-35.

Ganapathy-Kanniappan et al., "3-bromopyruvate: a new targeted antiglycolytic agent and a promise for cancer therapy." Curr Pharm Biotechnol. Aug. 2010;11(5):510-517.

Garcia-Roman et al., "VEGF secretion during hypoxia depends on free radicals-induced Fyn kinase activity in mast cells." BiochemBiophys Res Commun. Oct. 15, 2010;401(2):262-7.

Gilbert et al., "A phase I dose escalation and bioavailability study of oral sodium phenylbutyrate in patients with refractory solid tumor malignancies." Clinical Cancer Research Aug. 2001, 7:2292-2300.

Gore et al., Apr. 2002, Impact of prolonged infustions of the putative differentiating agent sodium phenylbutyrate on myelodysplastic syndromes and acute myeloid leukemia, Clinical Cancer Resarch, 8:963-970.

Gore, Steven D. et al., "Combined DNA Methyltransferase and Histone Deacetylase Inhibition in the Treatment of Myeloid Neoplasms, " Cancer Res 2006; 66:6361-6369.

Gorospe et al., "Up-regulation and functional role of p21Waf1/Cip1 during growth arrest of human breast carcinoma MCF-7 cells by phenylacetate." Cell Growth Differ. Dec. 1996;7(12):1609-15.

Granowitz et al., "Hyperbaric Oxygen Inhibits benign and malignant human mammary epithelial cell proliferation" Anticancer Res. Nov.-Dec. 2005;25(6B):3833-42.

Grimberg et al., "Role of insulin-like growth factors and their binding proteins in growth control and carcinogenesis." J Cell Physiol. Apr. 2000;183(1):1-9.

Guevara-Aguirre et al., "Growth hormone receptor deficiency is associated with a major reduction in pro-aging signalling, cancer, and diabetes in humans." Sci Transl Med. Feb. 16, 2011;3(70):70ra13.

Han et al., "Effect of glycolytic inhibitors on proliferation and apoptosis of pancreatic cancer cell under hypoxic condition", Chinese Journal of General Surgery, Mar. 2009, 18(3):243-246.

(56) References Cited

OTHER PUBLICATIONS

Han, S. et al., "Differentiation of human neurobl atoma by phenylacetate is mediated by peroxisome proliferator-activated receptor gamma," Cancer Res., May 15, 2001, vol. 61:3998-4002.

Haroon et al., "Lung metastic load limitation with hyperbaric oxygen," Undersee Hyperb Med., Mar.-Apr. 2007, 34(2):83-90.

Hashemzae et al., Aug. 2017, Anticancer and apoptosis-inducing effects of quercetin in vitro and in vivo, Oncology Reports, 38(2):819-828.

Hastak, K. et al., "Role of p53 and NF-kappaB in epigallocatechin-3-gallate-induced apoptosis of LNCaP cells," Oncogene, Jul. 31, 2003, 22:4851-4859.

Hong, J. et al., "Stability, cellular update, biotransformation, and efflux of tea polyphenol (-)-epigallocatechin-3-gallate in HT-29 human colon adenocarcinoma cells," Cancer Res Dec. 15, 2002, 62:7251-7246.

Hsu et al., "Chemoresistance of lung cancer stemlike cells depends on activation of Hsp27." Cancer. Apr. 1, 2011;117(7):1516-28.

Iannitti et al., 2011, Clinical and experimental applications of sodium phenylbutyrate, Drugs, 11(3):227-249.

Ishikawa, A. et al., "Smoking, alcohol drinking, green tea consumption and the risk of esophageal cancer in Japanese men." J Epidemiol, Sep. 2006, 16(5):185-192.

Israel, M. et al., "The metabolic advantage of tumor cells," Mol Cancer, Jun. 7, 2011, 10:70.

Jia et al., "Histone hyperacetylation is involved in the quercetin-induced human leukemia cell death", Pharmazie, 2008, 63:379-383.

Jian, L. et al., "Protective effect of green tea against prostate cancer: a case-control study in southeast China," Int J Cancer, Jan. 1, 2004, 108:130-135.

Jung et al., "EGCG, a major component of green tea, inhibits tumour growth by inhibiting VEGF induction in human colon carcinoma cells," Br J Cancer, Mar. 23, 2001, vol. 84.

Jung et al., "Inhibition of tumour invasion and angiogenesis by epigallocatechin gallate (EGCG), a major component of green tea," Int J Exp Pathol, Dec. 2001, 82:309-316.

Kanadaswami et al., "The antitumor activities of flavonoids." In Vivo. Sep.-Oct. 2005;19(5):895-909.

Kaplan et al., "The Insulin-like Growth Factor Axis and Prostate Cancer: Lessons from the Transgenic Adenocarcinoma of Mouse Prostate (TRAMP) Model 1" Cancer Res May 5, 1999 59; 2203.

Kawada et al., "Insulin-like Growth Factor I Secreted from Prostate Stromal Cells Mediates Tumor-Stromal Cell Interactions of Prostate Cancer" Cancer Res Apr. 15, 2006 66:4419-4425.

Khan et al., "Cancer Chemoprevention Through Dietary Antioxidants: Progress and Promise", Antioxidants and Redox Signaling, vol. 10, No. 3, pp. 475-510, 2008.

Kim et al., "Inhibition of vascular endothelial growth factor induced angiogenesis suppresses tumour growth in vivo" Nature, Apr. 29, 1993, 362:841-844.

Ko et al., "Advanced cancers: eradication in all cases using 3-bromopyruvate therapy to deplete Atp." BiochemBiophys Res Commun. Nov. 5, 2004;324(1):269-275.

Ko et al., "Glucose catabolismin the rabbit VX2 tumor model for liver cancer: characterization and targeting hexokinase," Cancer Lett. Nov. 8, 2001;173(1):83-91.

Koshikawa et al., "Reactive oxygen species generating mitochondrial DNA mutation up regulates hypoxia inducible factor-1 alpha gene transcription via phosphatidylinositol 3-kinase-Akt/protein kinase C/ histone deacetylase pathway" J Biol Chem. Nov. 27, 2009, 284(48):33185-94.

Kurahashi, N. et al., "Green tea consumption and prostate cancer risk in Japanese men: a prospective study," Am J Epidemiol, Jan. 1, 2008, 167(1):71-77.

Kurmasheva et al., "The insulin-like growth factor-1 receptor-targeting antibody, CP-751,871, suppresses tumor-derived VEGF and synergizes with rapamycin in models of childhood sarcoma." Cancer Res. Oct. 1, 2009;69(19):7662-71.

Kurzrock et al., Mar. 7, 2008, Targeted Cancer Therapy, Springer Science & Business Media, p. 362.

Lamson et al., "Antioxidants and Cancer III: Quercetin", Alternative Medicine Review, 5(3):196-208, 2000.

Lee et al., "Role of Bax in quercetin-induced apoptosis in human prostate cancer cells," Biochem Pharmacol. Jun. 15, 2008;75(12):2345-55.

Leroith et al., "The insulin-like growth factor system and cancer." Cancer Lett. Jun. 10, 2003;195(2):127-37.

Levy, J et al., "Tyrosine protein kinase activity in the DMBA-induced rat mammary tumor: inhibition by quercetin," Biochem Biophys Res Commun., Sep. 28, 1984, 123(3):1227-1233.

Li et al., "Synergistic epigenetic reactivation of estrogen receptor-.alpha. (ER.alpha.) by combined green tea polyphenol and histone deacetylase inhibitor in ER.alpha.-negative breast cancer cells". Molecular Cancer, Biomed Central, Oct. 14, 2010, 9(1):274.

Lin et al., Oct. 1, 2009, A phase I dose-finding study of 5-azacytidine in combination with sodium phenylbutyrate in patients with refractory solid tumors, Clin Cancer Res, 15(19);6241-6249.

Liu et al., "Transcriptional upregulation of TGF-alpha by phenylacetate and phenylbutyrate is associated with differentiation of human melanoma cells." Cytokine. Jul. 1995;7(5):449-56.

Major et al., "The Role of Octreotide in the Management of Patients with Cancer", Ontario Cancer Center, Practice Guideline Report 12-7, Aug. 2004, 37 pp.

Maki, "Small is beautiful: insulin-like growth factors and their role in growth, development, and cancer." J Clin Oncol. Nov. 20, 2010;28(33):4985-95. Epub Oct. 25, 2010.

Martinet et al., "Interpreting clinical assays for histone deacetylase inhibitors." Cancer Manag Res. 2011; 3: 117-141.

Mathupala et al., "Hexokinase II: cancer's double-edged sword acting as both facilitator and gatekeeper of malignancy when bound to mitochondria." Oncogene. Aug. 7, 2006;25(34):4777-86.

Mehrabian, S., "The study of antioxidant and anticarcinogenic green tea and black tea," Pak J Bioi Sci, Mar. 15, 2007, 10(6):989-991.

Michelakis, E.D. et al., "Metabolic Modulation of Glioblastoma with Dichloroacetate," Science Translational Medicine, Mar. 12, 2010, 2(31):989-994.

Michelakis, et al., "Dichioroacetate (DCA) as a potential metabolic-targeting therapy for cancer." Br J Cancer. Oct. 7, 2008;99(7):989-94.

Millauer et al., "Glioblastoma growth inhibited in vivo by a dominant-negative Flk-1 mutant." Feb. 10, 1994, Nature, 367:576-579.

Mokrzycki "Anti-atherosclerotic efficacy of quercetin and sodium phenylbutyrate in rabbits", Ann Acad Med Stetin, 2000; 46:189-200 (abstract).

Molnar et al., "Antitumor activity of flavonoids on NK/Ly ascites tumor cells." Neoplasma. 1981;28(1):11-18.

Monneret et al., "Histone deacetylase inhibitors", European Journal of Medicinal Chemistry, Jan. 2005, 40(1):1-13.

Moussa et al., "Hyperbaric oxygen as an adjuvant to cisplatin containing regimen: a companion to a hard journey" Proc Am Soc Clin Oncol 21: 2002 (abstr 2806).

Mukhtar, H. et al., "Tea polyphenols: prevention of cancer and optimizing health," Am J Clin Nutr, Jun. 2000, vol. 71.

Mulholland et al., "Pre-clinical and clinical study of QC12, a water-soluble, pro-drug of quercetin," Annals Oncol Feb. 2001 vol. 12 No. 2 pp. 245-248.

Murray, Quercetin, in How to Prevent and Treat Cancer with Natural Medicine Penguin, Nov. 4, 2003, Health and Fitness, 5 pp.

Mydio et al., "Prostate Cancer: Science and Clinical Practice (Google eBook)", Academic Press, p. 523, Jul. 11, 2003.

Nagano, J. et al., "A prospective study of green tea consumption and cancer incidence, Hiroshima and Nagasaki (Japan),"—Cancer Causes Control, Aug. 2001, 12:501-508.

Nam, S. et al., "Ester bond-containing tea polyphenols potently inhibit proteasome activity in vitro and in vivo," J Biol Chern, Apr. 20, 2001, 276:13322-13330.

Navarro-Peran et al., "The antifolate activity of tea catechins," Cancer Res, Mar. 15, 2005, 65:2059-2064.

Niedzwiecki et al., Sep. 9, 2016, Anticancer efficacy of polyphenols and their combinations, Nutrients, 8(9):1-17.

(56) References Cited

OTHER PUBLICATIONS

Nihal et al., "Anti-melanoma effects of vorinostat in combination with polyphenolic antioxidant Epigallocatechin-3-Gallate (EGCG)", Pharmaceutical Research, 27(6):1103-1114, Jun. 2010.
Pedersen PL, "Transport ATPases into the year 2008: a brief overview related to types, structures, functions and roles in health and disease." J Bioenerg Biomembr. Dec. 2007;39(5-6):349-355.
Pedersen, PL, "The cancer cell's "power plants" as promising therapeutic targets: an overview." J Bioenerg Biomembr. Feb. 2007;39(1):1-12.
Pelicano et al., 2008, Glycolysis inhibition for anticancer treatment, Oncogene, 25:4633-4646.
Phuphanich et al., "Oral sodium phenylbutyrate in patients with recurrent malignant gliomas: a dose escalation and pharmacologic study." Neuro Oncol 2005; 7(2):177-182.
Pisters, KM et al., "Phase I trial of oral green tea extract in adult patients with solid tumors," J Clin Oncol, Mar. 15, 2001, 19(6):1830-1838.
Plate et al., "Vascular endothelial growth factor is a potent tumour angiogenesis factor in human gliomas in vivo." Oct. 29, 1992, Nature, 359:845-848.
Pollak et al., "Insulin, insulin-like growth factors, insulin resistance, and neoplasia[1-4]" Am J Clin Nutr. Sep. 2007;86(3):s820-2.
Pollak, "Insulin and insulin-like growth factor signalling in neoplasia." Nat Rev Cancer. Dec. 2008;8(12):915-928.
Pollak, Michael N. et al., "Insulin-like Growth Factors and Neoplasia," Nature Reviews: Cancer, Jul. 2004, 4:505-518.
Prostate Cancer, Medline Plus, downloaded at http://www.nlm.nih.gov/medlineplus/print/ency/article/000380.htm, Nov. 9, 2009.
Qian et al., "Targeting tumor angiogenesis with histone deacetylase inhibitors: the hydroxamic acid derivative LBH589." Clin Cancer Res. Jan. 15, 2006;12(2):634-42.
Rokes et al., "Sorafenib Plus Valproic Acid for Infant Spinal Glioblastoma,"J Pediatr Hematol Concol, Aug. 2010, 32:511-514.
Roomi, MW. et al., "In vivo antitumor effect of ascorbic acid, lysine, proline and green tea extract on human prostate cancer PC-3 xenografts in nude mice: evaluation of tumor growth and immunohistochemistry," In Vivo, Jan.-Feb. 2005, 19:179-184.
Sasabe et al., "Mechanism of HIF-1alpha-dependent suppression of hypoxia-induced apoptosis in squamous cell carcinoma cells." Cancer Sci. Jul. 2005;96(7):394-402.
Scatena et al., "Glycolytic enzyme inhibitors in cancer treatment", Expert Opinion on Investigational Drugs, Informa Healthcare, 17(10):1533-1545, Oct. 2008.
Schwartz et al., "A combination of alpha lipoic acid and calcium hydroxycitrate is efficient against mouse cancer models: preliminary results." Oncol Rep. May 2010;23(5):1407-16.
Selvendiran, "Oxygnation inhibits ovarian tumor growth by downregulating STAT3 and cyclin-D1 expression" Cancer biol Ther, Aug. 2010, 10(4):386-390.
Shabbeer et al., "Focus on Deacetylation for Therapeutic Benefit", IDRUGS, Current Drugs Ltd, Feb. 2005, 8(2):144-154.
Shanafelt, Tait D. et al., "Phase I Trial of Daily Oral Polyphenon E in Patients with Asymptomatic Rai Stage 0 to II Chronic Lymphocytic Leukemia," Journal of Clinical Oncology, Aug. 10, 2009, 27(23):3808-3814.
Shankar, S. et al., "EGCG inhibits growth, invasion, angiogenesis and metastasis of pancreatic cancer," Front Biosci, Jan. 1, 2008, 13:440-452.
Sharma et al., "Molecular pathways in the chemosensitization of cisplatin by quercetin in human head and neck," Cancer BiolTher (2005) 4(9): 949-55.
Shoskes et al., "Quercetin in Men with Category III Chronic Prostatitis: A Preliminary Prospective, Double-Blind, Placebo-Controlled Trial", Urology 54 (6), pp. 960-963, 1999.
Shweiki et al., "Vascular endothelial growth factor induced by hypoxia may mediate hypoxia-initiated angiogenesis." Oct. 29, 1992, Nature, 359:843-845.
Staedler et al., "Drug combinations with quercetin: doxorubicin plus quercetin in human breast cancer cells." Cancer Chemother Pharmacol. Nov. 2011;68(5):1161-1172.
Sun, CL et al., "Green tea, black tea and breast cancer risk: a meta-analysisstudies," Carcinogenesis, Jul. 2006, 27(7):1301-1309.
Sung et al., "Combination of cytotoxic-differentiation therapy with 5-fluorouracil and phenylbutyrate in patients with advanced colorectal cancer." Anticancer Res. Mar.-Apr. 2007;27(2):995-1001.
Suzuki, Y. et al., "Green tea and the risk of breast cancer: pooled analysis of two prospective studies in Japan," Br J Cancer, Apr. 5, 2004, 90:1361-1363.
Takenouchi et al., "Studies on the metabolism of thioctic acid in skin diseases 2. Loading test of thioctic acid in various skin diseases" The Journal of Vitaminology 8, 99-114 (1962).
Tang et al., "The dietary bioflavonoid quercetin synergizes with epigallocathechin gallate (EGCG) to inhibit prostate cancer stem cell characteristics, invasion, migration and epithelial-mesenchymal transition." J Mol Signal. Aug. 18, 2010;5:14.
Tosetti, F., "Angioprevention: angiogenesis is a common and key target for cancer chemopreventive agents," FASEB, J Jan. 2002, vol. 16, 14 pp.
Troy et al., Remington: The Science and Practice of Pharmacy, p. 838, 2006.
Vaupel, "The Role of Hypoxia-Induced Factors in Tumor Progression" Oncologist. 2004;9 Suppl 5:10-17.
Wada et al., "A study on the metabolism of lipoic acid and lipoamide" The Journal of Vitaminology 7, 237-242 (1960).
Wang et al., "Co-treatment with quercetin to enhance the chemopreventive effect of green tea in prostate cancer", FASEB J., Apr. 2010, Meeting Abstract Supplement. Abstract.
Wang et al., Mar. 27, 2012, Quercetin increased the antiproliferative activity of green tea polyphenol (-)-epigallocatechin gallata in prostate cancer cells, Nutrition and Cancer, 64(4):580-587.
Wardell et al., "Glucose metabolism as a target of histone deacetylase inhibitors." Mol Endocrinol. Mar. 2009;23(3):388-401.
Wenzel et al., "Alpha-Lipoic acid induces apoptosis in human colon cancer cells by increasing mitochondrial respiration with a concomitant O2-*-generation" Apoptosis. Mar. 2005;10(2):359-368.
Wong et al., "Dichloroacetate induces apoptosis in endometrial cancer cells" Gynecol Oncol 109: 394-402.
Wu, AH. et al., "Green tea and risk of breast cancer in Asian Americans," Int J cancer, Sep. 10, 2003, 106:574-579.
Yang et al., "Cancer prevention by tea: animal studies, molecular mechanisms and human relevance," Nat Rev Cancer, Jun. 2009, 9:429-439.
Yang, CS., et al., "Inhibition of carcinogenesis by tea," Annu RevPharmacol Toxicol, 2002, 42:25-54.
Yang, Gong et al., "Prospective Cohort Study of Green Tea Consumption and Colorectal Cancer Risk in Women," Cancer Epidemiol Biomarkers Prev, Jun. 2007, 16:1219-1223.
Yoon, Joo-Heon et al., "Molecular Targets of Dietary Polyphenols with Anti-inflammatory Properties," Yonsei Med J., Oct. 31, 2005, 46(5):585-596.
Zhang et al., "Sodium 4-phenylbutyrate induces apoptosis of human lung carcinoma cells through activating JNK pathway." J Cell Biochem. Nov. 1, 2004;93(4):819-29.
Zhou et al., "Dietary polyphenol quercetin targets pancreatic cancer stem cells." Int J Oncol. Sep. 2010:37(3):551-561.
International Search Report & Written Opinion, dated Apr. 20, 2018, in International Patent Application No. PCT/US2018/19767.
Alexandrov et al., Aug. 2013, Signatures of mutational processes in human cancer, Nature, 500:415-420.
American Cancer Society, Nov. 1, 2008. Quercetin, 4 pp.
Ansel et al., 1999, Drug dosage and terminology, in Pharmaceutical Dosage Forms and Drug Delivery Systems, 7th Ed., Lippincott Williams & Wilkins, p. 48.
Arney, Oct. 24, 2014, Coming ever closer—first PARP inhibitor licensed in Europe, Cancer Research UK, https://news.cancerresearchuk.org/2014/10/24/coming-ever-closer-first-part-inhibitor-on-track-to-be-licensed-in-europe, 6 pp.

(56) References Cited

OTHER PUBLICATIONS

Azvolinsky, Mar. 16, 2012, MBCC: PARP inhibitors for breast cancer—which subpopulation to target?, https://www.cancernetwork.com/view/mbcc-parp-inhibitors-breast-cancerwhich-subpopulation-target, 3 pp.

Cairns et al., May 29, 2007, Metabolic targeting of hypoxia and HIF1 in solid tumors can enhance cytotoxic chemotherapy, Proc Natl Acad Sci USA 104(22):9445-9450.

Cao et al., 2008, Dichloroacetate (DCA) sensitizes both wild-type and over expressing Bcl-2 prostate cancer cells in vitro to radiation. Prostate 68:1223-1231.

Chen et al., 2011, Green tea epigallocatechin gallate enhances therapeutic efficacy of temozolomide in orthotopic mouse glioblastoma models, Cancer Letters, 302:100-108.

Ciesielski et al., 2020, Epigallocatechin-3-gallate (EGCG) alters histone acetylation and methylation and impacts chromatin architecture profile in human endothelial cells, Molecules, 25:2326.

Daruwalla et al., Nov. 7, 2006, Hyperbaric Oxygen Therapy for Malignancy, A review, World Journal of Surgery, 30:2112-2131.

Fang et al., Jan. 2007, Dietary Polyphenols May Affect DNA Methylation, J. Nutr., 137:223S-228S.

Glaser, 2007, HDAC inhibitors: Clinical update and mechanism-based potential, Biochem Pharmacol, 74(5):659-671.

Harris et al., Oct. 2016, Quercetin as an emerging anti-melanoma agent: a four-focus area therapeutic development strategy, Frontiers in Nutrition, 5(48), 14 pp.

Hu et al., 2016, Pharmacokinetics and antitumor efficacy of DSPE-PET2000 polymeric liposomes loaded with quercetin and tehmozolomide: analysis of their effectiveness in enhancing the chemosensitization of drug-resistant glioma cells, International Journal of Molecular Medicine, 37:690-702.

Lin et al., 2012, Inhibition of mitochondria- and endoplasmic reticulum stress-mediated autophagy augments temozolomide-induced apoptosis in glioma cells, PLOS One, 7(6):e38706.

Meng Mei, Jan. 15, 2006, Studies on the differentiation of human hepatocarcinoma cell induced by histone deacetylase inhibitors and its mechanism, China Doctoral Dissertations Full-Text Database, p. E-072-39.

Nagane, Jan. 2015, Dose-dense temozolomide: is it still promising? Neural. Med. Chir. 55(1):38-49.

vocabulary.com, Prophylaxis, dictionary definition, retrieved from http://www/vocabulary.com/dictionary/prophylaxis on Jun. 25, 2014, 4 pp.

Reagan-Shaw et al., Mar. 2007, Dose translation from animal to human studies revisited, The FASEB Journal, 22:659-661.

Schmutzler et al., 2000, Innovative strategies for the treatment of thyroid cancer, European Journal of Endocrinology, 143:15-24.

Sikora, Sep. 10, 2001, Cancer drug development in the post-genomic age, Current Science, 81(5):549-554.

Zhou et al., Dec. 31, 1992, Cancer change, abnormal change and sudden change, Research on Cancer Suppressor, 4(2):35-40.

Zips et al., 2005, New anticancer agents; in vitro and in vivo evaluation, In Vivo, 19:1-8.

Clesielski et al., 2020, Epigallocatechin-3-gallate (EGCG) alters histone acetylation and methylation and impacts chromatin architecture profile in human endothelial cells, Molecules, 25:2326.

Wang, Dec. 15, 2004, Studies on the apoptosis of NB4 cells induced by histone deacetylase inhibitors in combination with ATRA and As2O3 and its mechanism, China Master's Dissertations Full-Text Database, p. E072-35.

COMPOSITIONS, METHODS, SYSTEMS AND/OR KITS FOR PREVENTING AND/OR TREATING NEOPLASMS

PRIORITY AND CROSS REFERENCE TO RELATED APPLICATIONS

This application is the U.S. National Phase Application under 35 U.S.C. § 371 of International Application No. PCT/US2018/019767, filed Feb. 26, 2018, designating the U.S. and published in English as WO 2018/157081 A1 on Aug. 30, 2018, which claims the benefit of U.S. Provisional Application No. 62/464,296, filed on Feb. 27, 2017, which is hereby incorporated by reference in its entirety.

BACKGROUND

Field

The present disclosure is generally related to compositions, methods, systems and/or kits comprising, consisting of, or consisting essentially of, one or more anti-cancer response modulators in combination with one or more anti-cancer agents for preventing and/or treating neoplasms.

Certain embodiments of the present disclosure are related to compositions, methods, systems and/or kits comprising, consisting of, or consisting essentially of, one or more anti-cancer response modulators in combination with one or more anti-cancer agents for preventing and/or treating neoplasms that are resistant to the one or more anti-cancer agents.

Description of the Related Art

In 2007, the ten most commonly diagnosed cancers among men in the United States included cancers of the prostate, lung, colon, rectum, and bladder; melanomas of the skin; non-Hodgkin's lymphoma; kidney cancer, mouth and throat cancer, leukemia, and pancreatic cancer. In women, the most common cancers were reported as breast, lung and colon cancer. Overall, 758,587 men were told they had cancer and 292,853 men died from cancer in the U.S. in 2007.

In women, there has been a prevalence of 6,451,737 advanced cases reported in 2008 by the Surveillance, Epidemiology, and End Results (SEER) Program of the National Cancer Institute. In general there were 11,957,599 advanced cancer cases in the US reported in 2010 by the Centers for Disease Control and Prevention (CDC) and the incidence has been almost unchanged over the previous 8 years (482,000 cases in 2000 versus 456,000 cases in 2008). There has been an annual change of only approximately 0.6% in cancer incidence between the years of 1999 to 2008.

SUMMARY

In some embodiments, a pharmaceutical composition for prophylaxis, treatment or both of a neoplasm is provided comprising, consisting of, or consisting essentially of at least one anti-cancer agent, and a first anti-cancer response modulator, wherein the first anti-cancer response modulator is selected form the group consisting of quercetin, sodium phenyl butyrate (SPB) and epigallocatechin-3-gallate (EGCG). In some embodiments, the pharmaceutical composition further comprises, consists of, or consists essentially of, a second anti-cancer response modulator selected form the group consisting of quercetin, SPB and EGCG. In some embodiments, the pharmaceutical composition further comprises, consists of, consists essentially of, a third anti-cancer response modulator selected form the group consisting of quercetin, SPB and EGCG. In some embodiments of the pharmaceutical composition, the first anti-cancer response modulator is quercetin. In some embodiments of the pharmaceutical composition, the first anti-cancer response modulator is SPB. In some embodiments of the pharmaceutical composition, the first anti-cancer response modulator is EGCG. In some embodiments of the pharmaceutical composition, the second anti-cancer response modulator is quercetin. In some embodiments of the pharmaceutical composition, the second anti-cancer response modulator is SPB. In some embodiments of the pharmaceutical composition, the second anti-cancer response modulator is EGCG. In some embodiments of the pharmaceutical composition, the first, second and third anti-cancer response modulators are quercetin, SPB and EGCG. In some embodiments of the pharmaceutical composition, the at least one anti-cancer agent is cyclophosphamide. In some embodiments of the pharmaceutical composition, at least a portion of the pharmaceutical composition is formulated for IV administration or oral administration.

In some embodiments of the pharmaceutical composition, the amount of cyclophosphamide is about 50 mg to about 150 mg. In some embodiments of the pharmaceutical composition, the amount of quercetin is 0.1 g to 2.5 g. In some embodiments of the pharmaceutical composition, the quercetin is in solution at a concentration of 10 mg/ml to 500 mg/ml. In some embodiments of the pharmaceutical composition, the amount of SPB is 0.1 g to 40 g. In some embodiments of the pharmaceutical composition, the SPB is in solution at a concentration of 50 mg/ml to 500 mg/ml. In some embodiments of the pharmaceutical composition, the amount of EGCG is 0.1 g to 1.5 g. In some embodiments of the pharmaceutical composition, the EGCG is in solution at a concentration of 5 mg/ml to 50 mg/ml.

In some embodiments of the pharmaceutical composition, the anti-cancer agent and at least one anti-cancer response modulator are in a single dosage form for co-administration. In some embodiments of the pharmaceutical composition, the anti-cancer agent and at least one anti-cancer response modulator are in a single dosage form suitable for IV administration. In some embodiments of the pharmaceutical composition, the anti-cancer agent and at least one anti-cancer response modulator are in a single dosage form suitable for oral administration. In some embodiments of the pharmaceutical composition, the anti-cancer agent and at least one anti-cancer response modulator are in a separate dosage forms. In some embodiments of the pharmaceutical composition, the anti-cancer agent and at least one anti-cancer response modulator are each in dosage forms suitable for IV administration. In some embodiments of the pharmaceutical composition, the anti-cancer agent and at least one anti-cancer response modulator are each in dosage forms suitable for oral administration. In some embodiments of the pharmaceutical composition, either the anti-cancer agent or the at least one anti-cancer response modulator is in a dosage form suitable for oral administration and the other is in a dosage form for IV administration.

In some embodiments, the neoplasm is one or more of breast adenocarcinoma, pancreatic adenocarcinoma, lung carcinoma, prostate cancer, glioblastoma multiform, hormone refractory prostate cancer, solid tumor malignancies such as colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, and bladder cancer.

In some embodiments, the neoplasm is one or more of breast adenocarcinoma, pancreatic adenocarcinoma, lung carcinoma, prostate cancer, glioblastoma multiform, hormone refractory prostate cancer, solid tumor malignancies such as colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, bladder cancer, hematological malignancies, squamous cell carcinomas, breast cancer, astrocytomas, pilocytic astrocytoma, diffuse astrocytoma, anaplastic astrocytoma, and brain stem gliomas, glioblastomas, glioblastoma multiforme, meningioma, gliomas, ependymomas, oligodendrogliomas, and mixed gliomas, brain tumors, pituitary tumors, craniopharyngiomas, germ cell tumors, pineal region tumors, medulloblastomas, and primary CNS lymphomas.

In some embodiments, a kit for prophylaxis, treatment or both of a neoplasm is provided wherein the kit comprises, consists of, or consists essentially of, a pharmaceutical composition, wherein the pharmaceutical composition is in a single container. In some embodiments of the kit, each of the at least one anti-cancer agent and the one or more modulators are contained in a single container in a single dosage form. In some embodiments of the kit, each of the at least one anti-cancer agent and the one or more modulators are contained in separate sub-containers.

In some embodiments, use of any of the pharmaceutical compositions or kits disclosed herein for treatment, prevention or both of a neoplasm in a subject in need thereof is provided. In some embodiments, the neoplasm is likely to develop resistance, develops resistance, and/or is already resistant to the at least one anti-cancer agent. In some embodiments, the neoplasm is likely to develop resistance, develops resistance, and/or is already resistant to the one or more modulators.

In some embodiments, a method of prevention, treatment or both of a neoplasm is provided comprising, consisting of, or consisting essentially of, administering any of the compositions disclosed herein to a patient in need thereof. In some embodiments of the method, the pharmaceutical composition is administered to the subject IV, orally or both. In some embodiments of the method, the effect on the neoplasm is an improved result as compared to an effect on the neoplasm of either the at least one anti-cancer agent alone or the one or more modulators alone. In some embodiments of the method, the cyclophosphamide is administered at a dose of about 3 mg/kg to about 50 mg/kg. In some embodiments of the method, the quercetin is administered at a dose of 0.1 g to 2.5 g. In some embodiments of the method, the SPB is administered at a dose of 0.1 g to 40 g. In some embodiments of the method, the EGCG is administered at a dose is 0.1 g to 1.5 g.

In some embodiments, any of the compositions, kits, uses or methods disclosed herein induces apoptosis in vitro in at least one cancer cell line. In some embodiments, the induction of apoptosis by the composition is additive as compared to the induction of apoptosis of each of the anti-cancer agents and at least one modulators alone. In some embodiments, the induction of apoptosis by the composition is synergistic as compared to the induction of apoptosis of each of the anti-cancer agents and at least one modulator alone. In some embodiments, the composition, kit, use and/or method comprises, consists of, or consists essentially of cyclophosphamide as the at least one anti-cancer agent.

DETAILED DESCRIPTION

Figure 1:
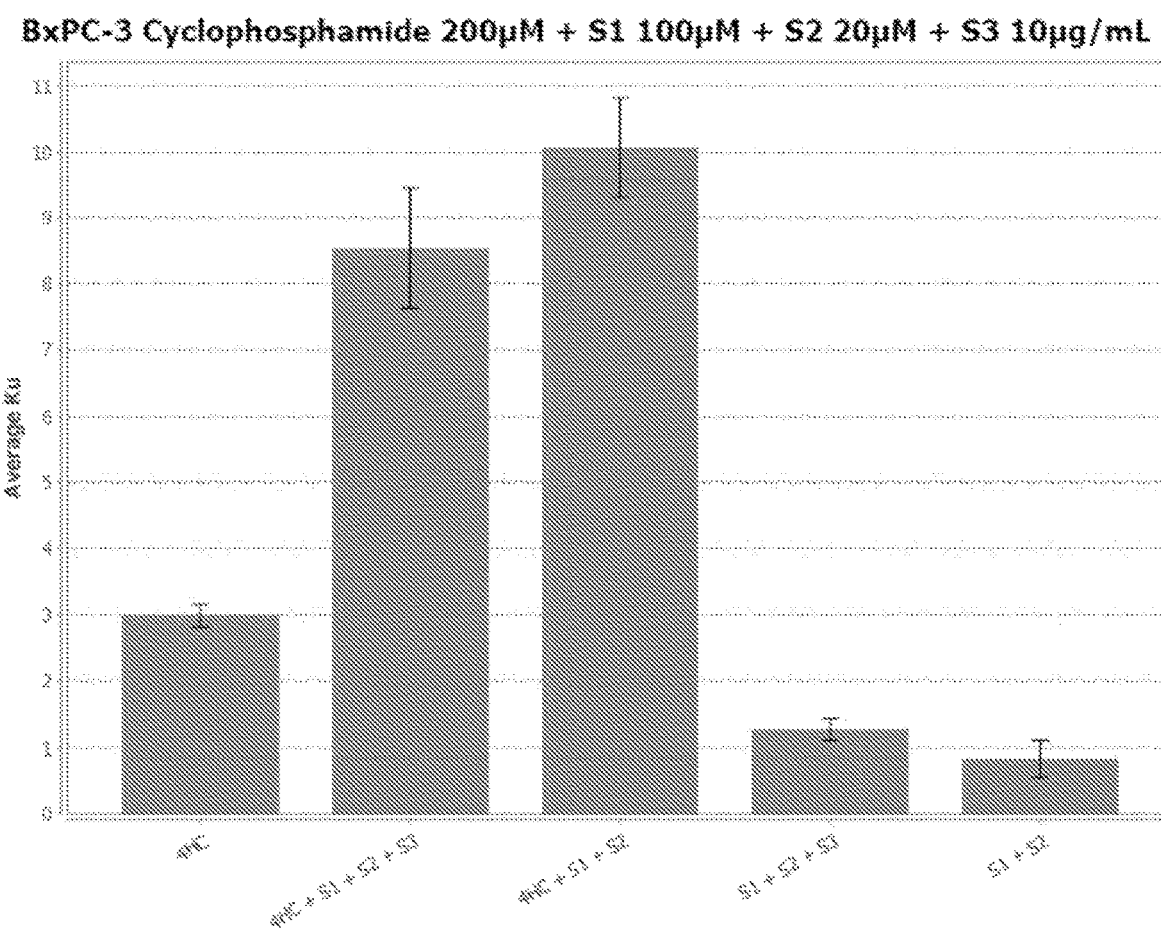
FIG. 1 shows a bar graph of the effect of cyclophosphamide alone, cyclophosphamide with quercetin (S1)+sodium phenyl butyrate (S2), and cyclophosphamide with S1+S2+epigallocatechin-3-gallate (S3) on BxPC-3 cell line. Also shown are the effects of S1+S2, and S1+S2+S3 without cyclophosphamide. Standard deviations are shown. All results are report in kinetic unit (KU).

Statistics show that deaths caused by advanced cancers of various types have not significantly changed since a decade ago. Indeed, in some cases (e.g., lung cancer) the death rate is rising, especially among women. Even as novel anti-cancer agents are introduced to the market for advanced stages of the disease, patient survival rates have remained essentially unchanged. Moreover, potential toxicity of many novel anti-cancer agents can be a devastating factor both for the clinician and the patient. Additionally, the development of resistance to anti-cancer agents is another cause for concern.

Therefore, compositions, methods, systems and/or kits comprising, consisting of, or consisting essentially of, one or more anti-cancer response modulators in combination with one or more anti-cancer agents for preventing and/or treating neoplasms are provided. In some embodiments, compositions, methods, systems and/or kits comprising, consisting of, or consisting essentially of, one or more anti-cancer response modulators in combination with one or more anti-cancer agents for preventing and/or treating neoplasms that are resistant to the one or more anti-cancer agents are provided. In some embodiments, the at least one anti-cancer agent is cyclophosphamide as the at least one anti-cancer agent Also provided herein are embodiments of case studies based on novel combinatorial therapies that provide superior clinical results in a variety of tumor types. In some embodiments, the combinatorial therapies are based on combinations of one or more modulators provided herein and one or more drugs for targeted therapies provided herein.

Patient Population

Provided herein are embodiments of compositions, methods, systems and/or kits useful for preventing and/or treating one or more neoplasms in patients. A neoplasm could be a tumor, a cancer, any new and/or abnormal growth resembling a tumor and/or cancer, or any combination thereof.

In some embodiments, a patient is administered one or more anti-cancer agents to prevent and/or treat a neoplasm. In some embodiments, the patient is naïve and never been previously treated with one or more anti-cancer agents. In some cases, the patient may initially respond to the one or more anti-cancer agents resulting in an initial regression of the neoplasm. However, the neoplasm may become resistant to the one or more anti-cancer agents resulting in a relapse. In some embodiments, relapse may also occur due to discontinuing treatment, in which case the relapsed neoplasm may or may not be sensitive to the one or more anti-cancer agents previously administered. Therefore, the patient may either be re-administered the same anti-cancer agent or a different anti-cancer agent. In some embodiments, the patient is initially treated with a first anti-cancer agent, but is subsequently treated with a different second anti-cancer agent. This may be due to several reasons including, but not limited to, development of resistance to the first anti-cancer agent, adverse effects of the first anti-cancer agent, etc.

Therefore, the embodiments of the compositions, methods, systems and/or kits provided herein are desirable for patients who are initially responsive but will eventually become non-responsive to one or more anti-cancer agents, or in patients who were initially responsive but have now become non-responsive to one or more anti-cancer agents. The embodiments are also desirable for patients who are non-responsive because they have a neoplasm that is resistant to one or more anti-cancer agents.

In some embodiments, the patient is a male or a female. A patient is typically human but animals other than human are also contemplated. Non-limiting examples of the animals other than human include without limitation domestic animals, pets, experimental animals, and/or commercially important animals.

Tumor and/or Cancer Types

Disclosed herein are non-limiting examples of neoplasms, which could be a tumor, a cancer, any new and/or abnormal growth resembling a tumor and/or cancer, or any combination thereof. In some embodiments, the neoplasm is a breast carcinoma or a breast adenocarcinoma, or any neoplasm associated with breast. In some embodiments, neoplasm is a non-small cell lung carcinoma or lung adenocarcinoma, or any neoplasm associated with lung. In some embodiments, the neoplasm is a uterine sarcoma, or any neoplasm associated with uterus. In some embodiments, the neoplasm is a pancreatic adenocarcinoma, or any neoplasm associated with pancreas. In some embodiments, the neoplasm is a malignant melanoma, or any neoplasm associated with skin. In some embodiments, the neoplasm is a glioblastoma, or any neoplasm associated with brain. In some embodiments, the neoplasm is related to one or more types of neoplasm provided herein.

In some embodiments, the neoplasm is likely to become resistant and/or is already resistant to one or more anti-cancer agents. Thus, the embodiments provided herein are particularly useful for preventing and/or treating neoplasm that are resistant to or are likely to become resistant to one or more anti-cancer agents. In some embodiments, the neoplasm is not resistant and/or is not likely to become resistant to one or more anti-cancer agents. Thus, the embodiments provided herein are useful for preventing and/or treating neoplasm that is not resistant and/or is not likely to become resistant to one or more anti-cancer agents by administering a minimum dose of one or more anti-cancer agents sufficient to prevent and/or treat the neoplasm.

Non-limiting examples of neoplasms include breast adenocarcinoma, pancreatic adenocarcinoma, lung carcinoma, prostate cancer, glioblastoma multiform, hormone refractory prostate cancer, solid tumor malignancies such as colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, bladder cancer, hematological malignancies, squamous cell carcinomas, breast cancer, glioblastoma, or any neoplasm associated with brain including, but not limited to, astrocytomas (e.g., pilocytic astrocytoma, diffuse astrocytoma, anaplastic astrocytoma, and brain stem gliomas), glioblastomas (e.g., glioblastomas multiforme), meningioma, other gliomas (e.g., ependymomas, oligodendrogliomas, and mixed gliomas), and other brain tumors (e.g., pituitary tumors, craniopharyngiomas, germ cell tumors, pineal region tumors, medulloblastomas, and primary CNS lymphomas) (See, cancercenter.com/brain-cancer/types/tab/overview/, which is hereby incorporated by reference in its entirety). In some embodiments, the neoplasm is related to one or more types of neoplasm provided herein.

Anti-Cancer Agents

As used herein an "anti-cancer agent" can be an anti-cancer agent, anti-tumor agent, anti-cancer drug and/or anti-tumor drug that slows the growth, stops the growth, causes a reduction in size, eliminates and/or prevents relapse of a neoplasm. In some embodiments, the anti-cancer agent is a pro-drug.

In some embodiments, the anti-cancer agents are well-known in the art and in some embodiments are approved for therapeutic use and/or use in clinical trials by government agencies (e.g., FDA, EMEA, etc.). The dosing, route of administration, efficacy against known neoplasm types, side/adverse effects, mechanism of action, etc. of the anti-cancer agents may also be well-known in the art. In other embodiments, the anti-cancer agent is a compound that is believed to have anti-cancer effects (e.g., without being limiting, in vitro, in vivo and/or ex vivo in a laboratory and/or in a human clinical trial), but is not yet approved by a government agency for the treatment of cancer.

Anti-Cancer Response Modulators

As used herein an "anti-cancer response modulator" (also referred to herein as "modulator") improves the anti-cancer effect of a known or a novel anti-cancer agent against a neoplasm when used in combination with one or more of the modulators disclosed herein. In some embodiments, the anti-cancer agent may not have any effect in the absence of the modulator. In some embodiments the anti-cancer agent improves the anti-cancer activity of the modulator. In some embodiments, the modulator improves the anti-cancer activity of the anti-cancer agent. In some cases, the two work in concert to improve the anti-cancer activity of each other. In some embodiments, the neoplasm is likely to develop resistance, develops resistance, and/or is already resistant to the known or a novel anti-cancer agent. In some embodiments, the neoplasm is likely to develop resistance, develops resistance, and/or is already resistant to one or more modulators.

Several embodiments of modulators are contemplated. Non-limiting examples of modulators include those that improve the effect of anti-cancer agents including, but not limited to, anti-cancer agents that are effective against one or more types of neoplasm but ineffective against one or more other types of neoplasm.

Thus, modulators are contemplated that improve the effect of anti-cancer agents in a patient who may be non-responsive to a particular anti-cancer agent or the anti-cancer agent may be ineffective in a patient with a particular type of neoplasm even before initiation of treatment with the anti-cancer agent. The modulator can improve the effect of anti-cancer agents in a patient who may initially be responsive to a particular anti-cancer agent or the anti-cancer agent may initially be effective in a patient with a particular type of neoplasm but may eventually become ineffective. In some embodiments, the modulator can improve the effect of anti-cancer agents in a patient with a relapse of the neoplasm.

Non-limiting examples of modulators include quercein, sodium phenyl butyrate (SPB) and epigallocatechin-3-gallate (EGCG). Other modulators are also contemplated. Quercetin is a flavonol found in many fruits, vegetables, leaves, and grains. It can be used as an ingredient in supplements, beverages, or foods. Quercetin is one of the most abundant dietary flavonoids with an average daily consumption of 25-50 mg. Sodium phenyl butyrate is a salt of an aromatic fatty acid, 4-phenylbutyrate (4-PBA) or 4-phenylbutyric acid and is classified by the FDA as an orphan drug for the treatment of urea cycle disorders. Epigallocatechin-3-gallate is a polyphenol and the most abundant catechin in tea. The modulators provided herein are non-toxic and/or minimally toxic with no and/or minimal side effects.

Dose of Modulator

The dose of modulators provided herein are exemplary and not intended to be limiting.

In some embodiments, quercetin is administered intravenously. The concentration of quercetin in a solution for intravenous administration is about 5 mg/ml to about 500 mg/ml. In some embodiments, the concentration of quercetin in a solution for intravenous administration is about 50 mg/ml. In some embodiments, quercetin is administered intravenously at a dose of about 0.05 g to about 10 g. In some embodiments, quercetin is administered intravenously at a dose of about 0.5 g to about 1 g. In some embodiments, quercetin is administered intravenously at a dose of about 0.05, 0.1, 0.2, 0.3, 0.4, 0.5, 0.6, 0.7, 0.8, 0.9, 1, 1.5, 2, 2.5 3, 3.5, 4, 4.5, 5, 5.5, 6, 6.5, 7, 7.5, 8, 8.5, 9, 9.5 or 10 g, or within a range defined by any two of the aforementioned values.

In some embodiments, quercetin is administered orally. The amount of quercetin in a composition for oral administration is about 100 mg to about 10 g. In some embodiments, quercetin is administered orally at a dose of about 0.5 g to about 4 g. In some embodiments, quercetin is administered orally at a dose of about 1 g. In some embodiments, quercetin is administered orally at a dose of about 0.05, 0.1, 0.2, 0.3, 0.4, 0.5, 0.6, 0.7, 0.8, 0.9, 1, 1.5, 2, 2.5 3, 3.5, 4, 4.5, 5, 5.5, 6, 6.5, 7, 7.5, 8, 8.5, 9, 9.5, 10, 15, 20, 25, 30, 35, 40, 45 or 50 g, or within a range defined by any two of the aforementioned values. In some embodiments, the composition for oral administration can be prepared into a solution for intravenous administration, wherein the concentration of quercetin is about 10 mg/ml to about 100 mg/ml. In some embodiments, quercetin is administered in a liposomal formulation. In some embodiments, quercetin is administered in a liposomal formulation at 50 mg a day. In some embodiments, quercetin is administered in a liposomal formulation at about 25 mg a day to about 75 mg a day. In some embodiments, quercetin is administered in a liposomal formulation at about 10, 15, 20, 25, 30, 35, 40, 45, 50, 55, 60, 65, 70, 75, 80, 85, 90, 95 or 100 mg a day, or within a range defined by any two of the aforementioned values.

In some embodiments, Quercetin by itself is not water soluble and therefore is administered in the oral dosage form. In some embodiments, Quercetin in the form of PG/PEG Propylene Glycol Quercetin (Quercetin PG) is water soluble and is used in the clinic as the IV dosage form.

In some embodiments, SPB is administered intravenously. The concentration of SPB in a solution for intravenous administration is about 20 mg/ml to about 2000 mg/ml. In some embodiments, the concentration of SPB in a solution for intravenous administration is about 200 mg/ml. In some embodiments, SPB is administered intravenously at a dose of about 0.5 g to about 100 g. In some embodiments, SPB is administered intravenously at a dose of about 1 g to about 10 g. In some embodiments, quercetin is administered intravenously at a dose of about 0.5, 0.6, 0.7, 0.8, 0.9, 1, 1.5, 2, 2.5 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95 or 100 g, or within a range defined by any two of the aforementioned values.

In some embodiments, SPB is administered orally. The amount of SPB in a composition for oral administration is about 0.1 g to about 50 g. In some embodiments, SPB is administered orally at a dose of about 0.5 g to about 1 g. In some embodiments, SPB is administered orally at a dose of 5 g to about 35 g. In some embodiments, SPB is administered orally at a dose of about 0.1, 0.2, 0.3, 0.4, 0.5, 0.6, 0.7, 0.8, 0.9, 1, 1.5, 2, 2.5 3, 3.5, 4, 4.5, 5, 5.5, 6, 6.5, 7, 7.5, 8, 8.5, 9, 9.5, 10, 15, 20, 25, 30, 35, 40, 45 or 50 g, or within a range defined by any two of the aforementioned values. In some embodiments, the composition for oral administration can be prepared into a solution for intravenous administration, wherein the concentration of SPB is about 20 mg/ml to about 2000 mg/ml.

In some embodiments, EGCG is administered intravenously. The concentration of EGCG in a solution for intravenous administration is about 5 mg/ml to about 100 mg/ml. In some embodiments, the concentration of EGCG in a solution for intravenous administration is about 20 mg/ml. In some embodiments, EGCG is administered intravenously at a dose of about 0.01 g to about 15 g. In some embodiments, EGCG is administered intravenously at a dose of about 0.1 g to about 1.5 g. In some embodiments, EGCG is administered intravenously at a dose of about 0.01, 0.05, 0.1 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 or 15 g, or within a range defined by any two of the aforementioned values.

In some embodiments, EGCG is administered orally. The amount of EGCG in a composition for oral administration is about 0.1 g to about 3 g. In some embodiments, EGCG is administered orally at a dose of about 0.2 g to about 1 g. In some embodiments, EGCG is administered orally at a dose of 0.5 g to about 2.5 g. In some embodiments, EGCG is administered orally at a dose of about 0.1 0.2, 0.3, 0.4, 0.5, 0.6, 0.7, 0.8, 0.9, 1, 1.5, 2, 2.5 or 3 g, or within a range defined by any two of the aforementioned values. In some embodiments, the composition for oral administration can be prepared into a solution for intravenous administration, wherein the concentration of EGCG is about 5 mg/ml to about 100 mg/ml. In some embodiments, a preventive dose of EGCG is about 0.27 g administered 2 times a day. In some embodiments, a preventive dose of EGCG is about 0.27 g administered 3 times a day.

Combinations

A surprising and unexpected anti-cancer effect was observed when one or more anti-cancer agents were used in combination with one or more modulators provided herein. The surprising and unexpected result was a better than expected result wherein the effectiveness of the one or more anti-cancer agents was improved when used in combination with one or more modulators as compared to the anti-cancer agent in the absence of the modulator(s). The potentiation was achieved by co-administering the one or more anti-cancer agents and one or more modulators.

Therefore, provided herein are combinations of one or more anti-cancer agents and one or more modulators. The one or more modulators can improve the effect of one or more anti-cancer agent against one or more neoplasm types provided herein. The potentiation can occur in several ways. Non-limiting examples include enhancing the effectiveness of an already effective anti-cancer agent, making an ineffective anticancer agent effective (the anticancer agent could also have been previously effective but become ineffective following long term and/or short term use in a patient), increasing the length of time for which an anti-cancer agent is effective, decreasing the effective dose of administration of the anti-cancer agent, decreasing the duration of time for which anti-cancer agent is administered, decreasing the frequency of administration of an anti-cancer agent, and/or enabling the administration of anti-cancer agent via a more amenable route.

The one or more anti-cancer agents can be provided at any dose, via any of the routes of administration, in any order of administration, at any frequency of administration, and/or any dosage form provided herein. Similarly, the one or more modulators can be provided at any dose, via any of the routes of administration, in any order of administration, at any frequency of administration, and/or any dosage form provided herein. Also, the combination of one or more anti-cancer agent and one or more modulators can be provided at any dose, via any of the routes of administration, in any order of administration, at any frequency of administration, and/or any dosage form provided herein.

Combinations can comprise, consist of, or consist essentially of, one or more anti-cancer agents and one or more modulators. In some embodiments, the combination comprises, consists of, consists essentially of, one or more anti-cancer agents and one modulator selected from the group consisting of quercetin, SPB and EGCG. In some embodiments, the modulator is quercetin. In some embodiments, the modulator is SPB. In some embodiments, the modulator is EGCG. In some embodiments, the combination comprises, consists of, or consists essentially of, one or more anti-cancer agents and at least one modulator. In some embodiments, the at least one modulator is selected from the group consisting of quercetin, SPB and EGCG. For example, in some embodiments, the combination can comprise, consist of, or consist essentially of the anticancer agent and quercetin, or the anti-cancer agent and SPB, or the anti-cancer agent and EGCG. In some embodiments, the combination comprises, consists of, consists essentially of, one or more anti-cancer agents and at least two modulators. In some embodiments, the at least two modulators are selected from the group consisting of quercetin, SPB and EGCG. For example, in some embodiments, the combination can comprise, consist of, or consist essentially of the anticancer agent and quercetin and SPB as the modulators, or the anticancer agent and quercetin and EGCG as the modulators, or the anticancer agent and SPB and EGCG as the modulators. In some embodiments, the anti-cancer agent is cyclophosphamide.

In some embodiments, the combination may comprise, consist of, or consist essentially of one or more additional modulators, for example, a third modulator selected from the group consisting of quercetin, SPB and EGCG. In some embodiments, if the first two modulators are quercetin and SPB, the third modulator is EGCG, if the first two modulators are quercetin and EGCG, the third modulator is SPB, and if the first two modulators are SPB and EGCG, the third modulator is quercetin. Therefore, for example, the combination can comprise, consist of, or consist essentially of the anticancer agent and quercetin, SPB and EGCG as the three modulators. In some embodiments, the anti-cancer agent is cyclophosphamide.

The potentiation can be additive or synergistic. A synergisitic effect is greater than an additive effect. An additive effect is observed when the potentiation is equal to the sum of the individual effects of the anti-cancer agent(s) and modulator(s). A synergistic effect is observed when the potentiation is greater than the sum of the individual effects of the anti-cancer agent and modulator(s). Synergistic effect, additive effect or both can be occur human patients, non-human patients, non-patient human volunteers, in vivo models, ex vivo models, in vitro models, etc.

Potentiation can range from about <1 to about 100 fold. In some embodiments, the synergistic effect is about 3 to about 30 fold. In some embodiments, the potentiation ranges from <1, 1, >1, 2, 3, 4, 5, 6, 7, 8, 9, 10, 20, 30, 40, 50, 60, 70, 80, 90, or 100 fold, or within a range defined by any two of the aforementioned values. In some embodiments, a synergistic effect allows for a reduction in the requirement of an anti-cancer agent to about 25% to about 75% of the recommended dose. In some embodiments, a synergistic effect allows for a reduction in the requirement of an anti-cancer agent to about 5, 10, 20, 30, 40, 50, 60, 70, 80, 90, or 95% of the recommended dose, or a value within a range defined by any two of the aforementioned values.

Figure 2:
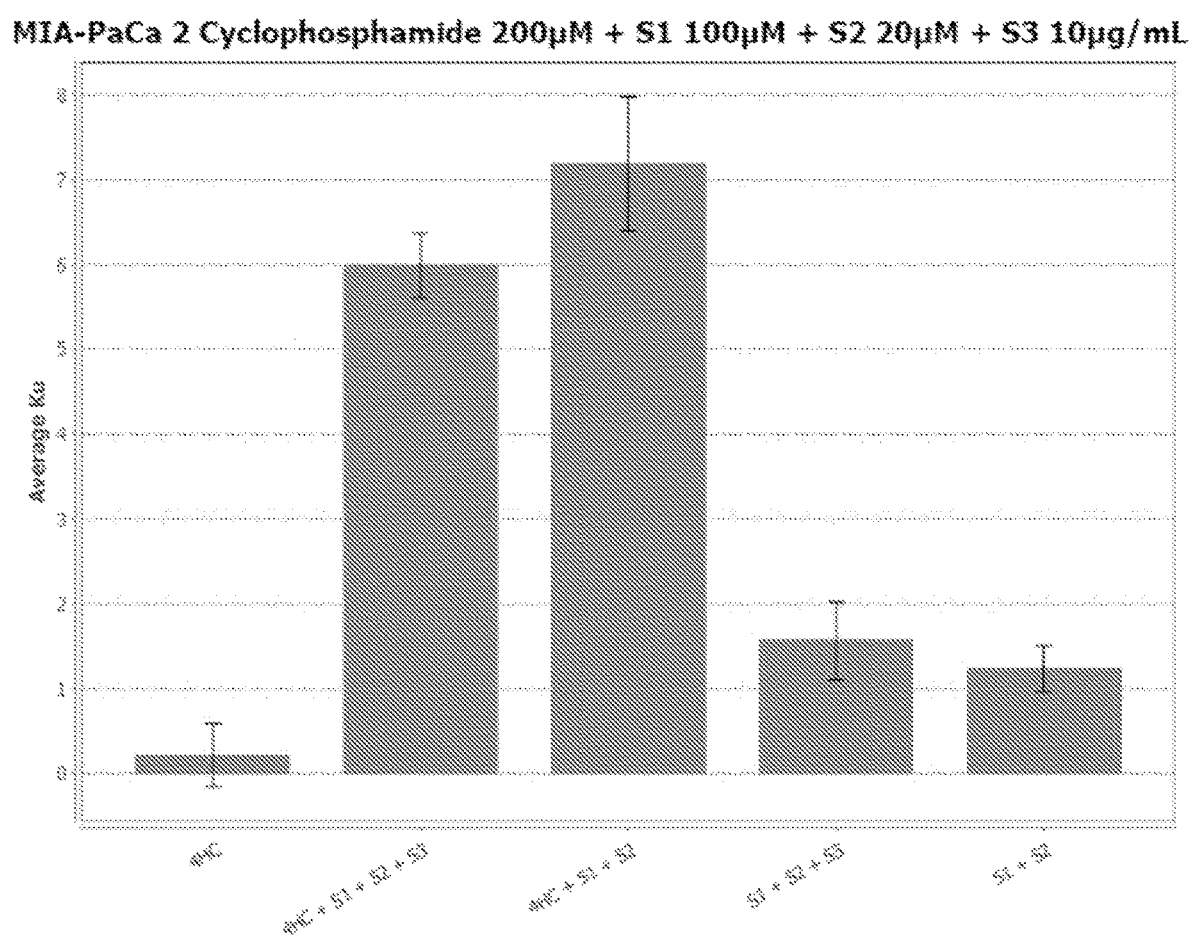
FIG. 2 shows a bar graph of the effect of cyclophosphamide alone, cyclophosphamide with S1+S2, and cyclophosphamide with S1+S2+S3 on MIA-PaCa 2 cell line. Also shown are the effects of S1+S2, and S1+S2+S3 without cyclophosphamide. Standard deviations are shown. All results are report in kinetic unit (KU).

For example, the combination of cyclophosphamide with quercetin and SPB can produce a synergistic effect on a neoplasm that is resistant to cyclophosphamide alone (e.g., as shown in FIG. 2, the synergistic effect of the combination of cyclophosphamide with quercetin and SPB on the pancreatic adenocarcinoma cell line MIA-PaCa 2 is 30 fold as compared to the cyclophosphamide alone or the combination of quercetin and SPB alone).

In some embodiments, additive and/or synergistic or sustained response to a combinational therapy is observed. In some embodiments, "combination therapy" is intended to encompass administration of these therapeutic agents in a sequential manner, wherein each therapeutic agent is administered at a different time, as well as administration of these therapeutic agents, or at least two of therapeutic agents concurrently, or in a substantially simultaneous manner. Simultaneous administration can be accomplished, for example, by administering to the subject a single dosage form, for example, a solution, pill or capsule, having a fixed ratio of each therapeutic agent or in multiple, single dosage forms for each of therapeutic agents. Sequential or substantially simultaneous administration of each therapeutic agent can be effected by any appropriate route including, but not limited to, oral routes, intravenous routes, intramuscular routes, and direct absorption through mucous membrane tissues.

In some embodiments, mixtures of compositions of the present invention can also be administered to the patient as a simple mixture or in suitable formulated pharmaceutical compositions. In some embodiments, combination therapy can be achieved by administering two or more agents, e.g., two or more other therapeutic agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

The potentiation can be measured in one or more assays that measure effects such as apoptosis, cellular metabolic changes, cellular morphological changes, etc., or other effects that would be well-known to one of ordinary skill in the art. In some embodiments, the combination of anti-cancer agent(s) and one or more modulators causes an induction of apoptosis, which can be measured using the MiCK® assay (Example 1). In some embodiments, the modulator can suppress angiogenesis within/around the neoplasm. For example, Quercetin causes suppression of angiogenesis in glioma cells.

In some embodiments, the one or more modulators provided herein are effective as anticancer agents without the presence of an anti-cancer agent. Thus, in some embodiments, the one or more modulators provided herein are independently effective as anti-cancer agents, i.e., without co-administration of one or more anti-cancer agents.

However, when the one or more modulators provided herein are administered in combination with one or more anti-cancer agents, a synergistic anti-cancer effect is observed. Thus, in some embodiments, a synergistic anti-cancer effect is observed when the one or more modulators provided herein are co-administered with the one or more anti-cancer agents provided herein. For example, a synergistic anti-cancer effect is observed when quercetin (e.g. as quercetin PG is co-administered with cyclophosphamide (See, Examples 5-7).

Route of Administration

The route of administration of the modulator(s) and anti-cancer agent(s) can be determined by one of ordinary skill in the art based on the circumstances. Several non-limiting routes of administrations are possible including parenteral, subcutaneous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal.

Any route of administration provided herein can be used for the combination of anti-cancer agent(s) and modulator(s) or for the individual components of the combination. For example, the combination of anti-cancer agent and modulator can be administered intravenously, orally or both. In some embodiments, one or more components in the combination can be administered via one route (e.g., intravenously) and the other components can be administered via a different route (e.g., orally). In some embodiments, all components in the combination are administered via the same route (e.g., either intravenously or orally). The anti-cancer agent and modulators can be administered via any combination of intravenous and oral routes as shown in the non-limiting examples of Table 1 and Table 2.

TABLE 1

Combinations comprising, consisting of, or consisting essentially of, one anti-cancer agent and two modulators (S1, S2)

| | Route of administration | | |
|---|---|---|---|
| Combination | Anti-cancer agent | S1 | S2 |
| 1 | IV | IV | IV |
| 2 | Oral | IV | IV |
| 3 | IV | Oral | IV |
| 4 | IV | IV | Oral |
| 5 | Oral | Oral | IV |
| 6 | Oral | IV | Oral |
| 7 | IV | Oral | Oral |
| 8 | Oral | Oral | Oral |

TABLE 2

Combinations comprising, consisting of, or consisting essentially of, one anti-cancer agent and three modulators (S1, S2, S3)

| | Route of administration | | | |
|---|---|---|---|---|
| Combination | Anti-cancer agent | S1 | S2 | S3 |
| 1 | IV | IV | IV | IV |
| 2 | Oral | IV | IV | IV |
| 3 | IV | Oral | IV | IV |
| 4 | IV | IV | Oral | IV |
| 5 | IV | IV | IV | Oral |
| 6 | Oral | Oral | IV | IV |
| 7 | Oral | IV | Oral | IV |
| 8 | Oral | IV | IV | Oral |
| 9 | IV | Oral | Oral | IV |
| 10 | IV | Oral | IV | Oral |
| 11 | IV | IV | Oral | Oral |
| 12 | Oral | Oral | Oral | IV |
| 13 | IV | Oral | Oral | Oral |
| 14 | Oral | IV | Oral | Oral |
| 15 | Oral | Oral | IV | Oral |
| 16 | Oral | Oral | Oral | Oral |

In some embodiments of Table 1 and Table 2, the anti-cancer agent is cyclophosphamide, S1 is quercetin, S2 is SPB, and S3 is EGCG.

Order of Administration

Any order of administration can be used for the one or more anti-cancer agents and one or more modulators in a combination. For example, the one or more anti-cancer agents and the one or more modulators in the combination can be administered simultaneously or sequentially. For example, all components of the combination are administered simultaneously, or only some of the components of the combination are administered simultaneously and the rest are administered sequentially. In some embodiments, none of the components are administered simultaneously, i.e., all the components are administered sequentially. When administering sequentially, any order of administration can be used. For example, when administering a combination of one anti-cancer agent and two modulators, the anti-cancer agent can be administered first followed by the two modulators either simultaneously or sequentially in any order, or the two modulators can be administered first either simultaneously or sequentially in any order followed by the anti-cancer agent, or one of the modulator each can be administered before and after the administration of the anti-cancer agent. Additional orders of administration are possible and contemplated when the combination comprises, consists of, consists essentially of, additional components, for example, a third modulator.

Frequency of Administration

Frequency of administration of the anti-cancer agent is as known in the art. Frequency of administration of the anti-cancer agent can be varied depending various parameters such as level of potentiation, prognosis following administration of a combination provided herein, patient compliance, side effects, etc., for example, daily, weekly, biweekly, monthly, bimonthly, or as is known in the art. Modulators can be administered along with the anti-cancer agent daily, weekly, biweekly, monthly, bimonthly, less frequently compared to the anti-cancer agent, or more frequently compared to the anti-cancer agent.

Administration can be daily, or 1, 2, 3, 4, 5, 6 or more times weekly, or more or less frequently as required. Administration can be provided as a single dose or as divided doses, such that a daily dose may be given in 2, 3, 4, or more portions in a single day.

Co-administration of the components of a combination may comprise administering the components simultaneously, or within about 1, 5, 15, 30, 45 or 60 minute of one another, or within any range defined by the aforementioned values. Co-administration of the components of a combination may comprise, consist of, or consist essentially of, administering the components within about 1 hour to within about 6 hours of one another, or within any range defined by the aforementioned values.

Pharmaceutical Formulations

In some embodiments, pharmaceutical formulations for prophylaxis, treatment or both of a neoplasm are provided. The formulation can be a single composition for co-administration comprising, consisting of, or consisting essentially of, at least one anti-cancer agent and one, two, three or more modulators. In some embodiments, the formulation comprises, consists of, consists essentially of, more than one composition, e.g. the anti-cancer agent in one dosage form, and the one or more modulators in a second, third or fourth dosage form. Several compositions are contemplated. The type of composition to be administered can be determined by one of ordinary skill in the art based on the circumstances under which administration is desired.

The compositions provided herein comprise, consist of, or consist essentially of, active ingredients, inactive ingredients, excipients, additives, and/or pharmaceutically acceptable carriers. Examples of additives include natural polymer compounds, inorganic salts, binders, lubricants, disintegrants, surfactants, thickeners, coating agents, pH adjusters, antioxidants, flavoring agents, preservatives, and colorants among others. Examples of other pharmaceutically acceptable carriers include liquid carriers such as water, alcohol, emulsion, and solid carriers such as gel, powder, etc. Standard pharmaceutical formulation techniques and ingredients can be used, such as those disclosed in Remington's The Science and Practice of Pharmacy, 21st Ed., Lippincott Williams & Wilkins (2005), which is hereby incorporated by reference in its entirety.

Compositions for intravenous administration comprise, consist of, or consist essentially of, excipient and pharmaceutically acceptable carries including one or more of sodium chloride, dextrose, and sterile water. Compositions can comprise, consist of, or consist essentially of, aqueous isotonic sterile injection solutions, which can comprise, consist of, or consist essentially of, one or more of antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Compositions for oral administration can be any dosage form that is suitable for oral ingestion, for example, liquid compositions such as elixir, suspension, syrup, emulsion, ampoule, etc., solid compositions such as gel, gum, drop, powder, granule, pill, sugar-coated tablet, film-coated tablet, capsule, package agent, etc. Also contemplated are sustained-release compositions such as gel-coated compositions, multi-coated compositions, localized release compositions.

In some embodiments, the compositions are administered by intravenous infusion. The compositions can be presented in unit-dose or multi-dose sealed containers, such as ampules and/or vials. Injection solutions and suspensions can be prepared from sterile powders, granules, and/or tablets. In some embodiments, the compositions to be administered can be formulated as pharmaceutical formulations for delivery via one or more of the routes provided herein.

A composition can comprise, consist of, or consist essentially of, a combination of one or more anti-cancer agents and one or more modulators, wherein the one or more anti-cancer agents and one or more modulators can be present in any dosage form. For example, in a composition comprising a combination of one anti-cancer agent and two modulators, all three components can be in the same dosage form (e.g., for intravenous administration or for oral administration), or one of the components in the combination can be of one dosage form (e.g., for intravenous administration or for oral administration) and other two component in the combination can be of a different dosage form (e.g., for intravenous administration or for oral administration). In some embodiments, all three components in the combination may be of a different dosage form (e.g., for intravenous administration, for oral administration, and a third dosage form). In some embodiments, when the combination additionally comprises, consists of, or consists essentially of, a third modulator, the dosage form of the third modulator may be the same as one of the other components in the combination or the third modulator may be present in a different (e.g., fourth) dosage form. The various dosage forms can be administered in an order as disclosed herein.

In some embodiments, the pharmaceutical formulation is formulated as one or more of a nanoparticle formulation, a liposomal formulation, or folic acid receptor conjugates. Nanoparticle formulations have many advantages over traditional dosage forms, such as enhanced dissolution properties and potential for efficient intracellular delivery of drugs. Nanoparticles have unique physical and chemical properties that offer several advantages as drug delivery carriers, or 'nano-carriers.' Nanoparticles-based composition for detection and/or treatment of cancers can comprise nanoparticles in the form of, without limitations, quantum dots, magnetic nanoparticles, gold nanoshells (which are useful in detecting tumors and metastasis in many solid tumors), poly (lactide-co-glycolide) (PLGA)-based nanoparticles (e.g., PLGA/montmorillonite (PLGA/MMT) nanoparticles, Vitamin E-TPGS-emulsified PLGA nanoparticles, PLGA-mPEG nanoparticles), dendrimers, and SPIO and USPIO nanoparticles. See, Mousa S. A. and Bharali D. J., *Nanotechnology-Based Detection and Targeted Therapy in Cancer: Nano-Bio Paradigms and Applications*, Cancers (Basel), Vol. 3, No. 3, pp. 2888-2903, September 2011, which is hereby incorporated by reference in its entirety. Other nanoparticle-based examples are provided in Bharali D. J. and Mousa S. A., *Emerging nanomedicines for early*

*cancer detection and improved treatment: current perspective and future promise*, Pharmacology & Therapeutics, Vol. 128, No. 2, pp. 324-335, November 2010, and Bharali D. J., et al., *Nanoparticles and cancer therapy: a concise review with emphasis on dendrimers*, International Journal of Nanomedicine, Vol. 4, pp. 1-7, Apr. 1, 2009, which are hereby incorporated by reference in their entirety. Pharmaceutical compositions can also be formulated as nanomicelles-based compositions, for example, as provided in U.S. Pat. No. 9,308,270 B2, which is hereby incorporated by reference in its entirety. Folic acid receptor conjugates based on a conjugating a molecule/drug with folic acid to form a "folate conjugate." Owing to the naturally high affinity of folate for the folate receptor protein commonly expressed on the surface of many human cancers, folate conjugates bind tightly to the folate receptor protein and trigger cellular uptake via endocytosis. Diverse molecules/drugs can be successfully delivered inside folate receptor protein expressing cells and tissues. Liposomal formulations comprise liposomes that are used as vehicles for administration of drugs. Liposomes are most often composed of phospholipids, especially phosphatidylcholine, but may also include any lipids that are compatible with a lipid bilayer structure (e.g., as egg phosphatidylethanolamine). A liposomal formulation can comprise liposomes that may employ surface ligands for attaching to unhealthy tissue. The major types of liposomes are multilamellar vesicle with several lamellar phase lipid bilayers, small unilamellar liposome vesicle with one lipid bilayer, large unilamellar vesicle, and cochleate vesicle.

For example, in a composition comprising a combination of cyclophosphamide as the anti-cancer agent and quercetin and SPB as the two modulators, all three can be in an intravenous or oral dosage form, cyclophosphamide can be in an intravenous dosage form and quercetin and SBP can be in an oral dosage form, or cyclophosphamide can be in oral dosage form and quercetin and SPB can be in an intravenous dosage form. In some embodiments, the combination may comprise, consist of, or consist essentially of, a third modulator (e.g., EGCG) that is in the same or a different dosage form than the anti-cancer agent and/or one or more of the modulators.

Kits

Inasmuch as it may desirable to administer one or more combinations provided herein, for example, for the purpose of preventing and/or treating a neoplasm, it is within the scope of the present disclosure to provide the components of a combination as a kit such that the components of the combination are suitable for co-administration.

A kit comprising, consisting of, or consisting essentially of, one or more anti-cancer agents to be used in combination with one or more modulators is provided.

In some embodiments, the kit comprises, consists of, or consists essentially of, one anti-cancer agent to be used in combination with two modulators. In some embodiments, the kit further comprises, consists of, or consists essentially of, a third modulator. Thus, the kit comprises, consists of, or consists essentially of, one anti-cancer agent to be used in combination with three modulators.

The components can be separately provided such as in separate containers, or in separate compartments of a divided bottle or divided foil packet (e.g., a blister pack used for the packaging of tablets, capsules, etc.).

The kit is particularly suitable for administering different dosage forms, for example, oral and intravenous, for administering the components at different dosage intervals, and/or for titration of components against one another. The kit typically comprises, consists of, consists essentially of, directions for administration and may additionally be provided with a memory aid to ensure compliance.

The components in the kit may exist in dissolved form, undissolved form or a combination thereof. If present in undissolved form, the undissolved component may be combined with another component present in a dissolved form in a specific stoichiometric amount prior to use. If all the components are present in an undissolved form, the components can either be administered as such (e.g., orally) or dissolved into a solvent (e.g., water) prior to administration (e.g., intravenously).

In some embodiments, the kit comprises, consists of, consists essentially of, cyclophosphamide as the anti-cancer agent to be used in combination with quercetin and SPB as the two modulators. In some embodiments, the kit can comprise EGCG as the third modulator. Thus, the kit comprises, consists of, consists essentially of, cyclophosphamide as the anti-cancer agent to be used in combination with quercetin, SPB and EGCG as the three modulators.

Cyclophosphamide

In any of the embodiments of the methods, systems and/or kits disclosed herein, the embodiments of the compositions can be used for the treatment of diseases, including but not limited to types of cancers disclosed herein and any other diseases or cancers known in the art to be treated by the disclosed compounds. In any of the embodiments of the compositions, methods, systems and/or kits disclosed herein, the anti-cancer agent can be cyclophosphamide, also known as cytophosphane. 4HC is a metabolite of Cytoxan. Cyclophosphamide is used to treat cancers, autoimmune disorders and AL amyloidosis. As a prodrug, it is converted by liver cytochrome P450 (CYP) enzymes to form the metabolite 4-hydroxycyclophosphamide that has chemotherapeutic activity.

The dosing of cyclophosphamide varies depending on, among other aspects, patient age, route of administration, neoplasm type, etc. Cyclophosphamide is typically administered intravenously, orally or both in adult and pediatric patients.

When used as the only oncolytic drug therapy, intravenous dosing for adult and pediatric patients with malignant diseases, the initial course of cyclophosphamide for patients with no hematologic deficiency usually consists of 40 mg/kg to 50 mg/kg in divided doses over a period of 2 to 5 days. Other intravenous regimens include 10 mg/kg to 15 mg/kg every 7 to 10 days, or 3 mg/kg to 5 mg/kg twice weekly. Cyclophosphamide dosing is known to those of skill in the art.

Oral cyclophosphamide dosing is usually in the range of 1 mg per kg per day to 5 mg per kg per day for both initial and maintenance dosing. Oral dosing for minimal change nephrotic syndrome in pediatric patients consists of 1 mg/kg/day to 5 mg/kg/day, or 2 mg/kg/day for 8 to 12 weeks (maximum cumulative dose 168 mg per kg) is recommended. Treatment beyond 90 days increases the probability of sterility in males.

In some embodiments, the frequency of administration is daily. In some embodiments, the frequency of administration is once a week. In some embodiments, the frequency of administration is once every two weeks. In some embodiments, the frequency of administration is once every three weeks. In some embodiments, the frequency of administration can be dose is once every 6 months. In some embodiments, the frequency of administration can be adjusted as desired by one of ordinary skill in the art based on parameters such as the type of drug, the route of administration, the disease, and the like.

Other regimens of intravenous and oral cyclophosphamide have also been reported. Dosages must be adjusted in accord with evidence of antitumor activity, leukopenia or both. Total leukocyte count is a good, objective indicator for regulating dosage.

Cyclophosphamide is effective alone for susceptible malignancies. However, cyclophosphamide is more frequently used concurrently or sequentially with other antineoplastic drugs. When cyclophosphamide is included in combined cytotoxic regimens, the doses of cyclophosphamide as well as that of the other drugs are adjusted accordingly as known to those of skill in the art.

The compositions, methods, systems and/or kits provided herein can be used for treating neoplasms, non-limiting examples of which are malignant lymphomas (Stages III and IV of the Ann Arbor staging system), Hodgkin's disease, lymphocytic lymphoma (nodular or diffuse), mixed-cell type lymphoma, histiocytic lymphoma, Burkitt's lymphoma, multiple myeloma, leukemias including but not limited to chronic lymphocytic leukemia, chronic granulocytic leukemia (it is usually ineffective in acute blastic crisis), acute myelogenous and monocytic leukemia, acute lymphoblastic (stem-cell) leukemia (cyclophosphamide given during remission is effective in prolonging its duration), mycosis fungoides (advanced disease), neuroblastoma (disseminated disease), adenocarcinoma of the ovary, retinoblastoma, carcinoma of the breast, and biopsy-proven minimal change nephrotic syndrome in pediatrics patients who failed to adequately respond to or are unable to tolerate adrenocorticosteroid therapy. Additional FDA approved and off label indications for Cyclophosphamide (Cytoxan) are ovarian cancer, retinoblastoma, breast cancer, multiple myeloma, Ewing sarcoma, rhabdomyosarcoma, endometrial cancer and lung cancer.

Provided herein are combinations comprising cyclophosphamide and at least one modulator selected from the group consisting of quercetin, SPB and EGCG. In some embodiments, the combination comprises, consists of, consists essentially of, cyclophosphamide and quercetin. In some embodiments, the combination comprises, consists of, consists essentially of, cyclophosphamide and SPB. In some embodiments, the combination comprises, consists of, consists essentially of, cyclophosphamide and EGCG. The combinations can comprise cyclophosphamide, quercetin, SPB and EGCG at any of the doses provided herein for each.

Also provided are combinations comprising cyclophosphamide and at least two modulators selected from the group consisting of quercetin, SPB and EGCG. In some embodiments, the combination comprises, consists of, consists essentially of, cyclophosphamide, quercetin and SPB. In some embodiments, the combination comprises, consists of, consists essentially of, cyclophosphamide, quercetin and EGCG. In some embodiments, the combination comprises, consists of, consists essentially of, cyclophosphamide, SPB and EGCG. The combinations can comprise cyclophosphamide, quercetin, SPB and EGCG at any of the doses provided herein for each.

In some embodiments, the combination comprises, consists of, consists essentially of, cyclophosphamide and three modulators. In some embodiments, the combination comprises, consists of, consists essentially of, cyclophosphamide, quercetin, SPB and EGCG. The combinations can comprise cyclophosphamide, quercetin, SPB and EGCG at any of the doses provided herein for each. In some embodiments, the combination comprises, consists of, consists essentially of, one or more additional anti-cancer agents and one or more additional modulators.

Non-limiting examples of cyclophosphamide doses are as follows. Oral cyclophosphamide can be used at doses of about 50 mg per day to about 150 mg per day to an "on" and "off" schedule of 1-14 days "on" and 14-28 days "off" in 28 day schedule, as a metronomic dose. Standard dose of cyclophosphamide for oral administration for initial and maintenance dose in leukemias is about 1 mg/kg to about 5 mg/kg. Intravenous dose of cyclophosphamide include about 40 mg/kg to about 50 mg/kg (total course dose) in divided doses given over 2 to 5 days. Other IV regimens include cyclophosphamide at about 10 mg/kg to about 15 mg/kg every 7 to 10 days or cyclophosphamide at about 3 mg/kg to about 5 mg/kg twice weekly. Routinely, cyclophosphamide is used IV at about 440 mg/m2 to about 600 mg/m2, up to about 4 g/m2 (about 10 mg/kg to about 15 mg/kg), and orally at about 50 mg to about 150 mg (average 100 mg/m2).

Doses of quercetin, SPB and EGCG for intravenous administration can be any one of the doses provided herein. For example, doses of quercetin for intravenous administration include, without limitations, 0.5 g to 1 g. Doses of SPB for intravenous administration include, without limitations, 5 g to 10 g. Doses of EGCG for intravenous administration include, without limitations, 0.1 g to 1.5 g.

In some embodiments, the any of the combinations herein are provided as compositions, methods and/or kits for preventing neoplasms in patients and/or treating neoplasms in patients. Any of the doses, routes of administration, frequency of administration, sequence of administration, etc. provided herein can be used for the components of the combinations.

The dose, route of administrations, mechanism of action, etc. of cyclophosphamide are well-known in the art. The dose of cyclophosphamide can be varied depending on, among other aspects, patient age, route of administration, neoplasm type, etc.

Additional Embodiments

In some embodiments, the combinations in the compositions, and the compositions for the kits, uses and/or methods described herein comprise, consist of, or consist essentially of, Quercetin+cyclophosphamide, wherein Quercetin is administered intravenously, wherein the concentration of Quercetin in a solution for intravenous administration is about 5 mg/ml to about 500 mg/ml, and wherein cyclophosphamide is administered intravenously, wherein the cyclophosphamide is in a solution for intravenous administration.

In some embodiments, the combinations in the compositions, and the compositions for the kits, uses and/or methods described herein comprise, consist of, or consist essentially of, Quercetin+cyclophosphamide, wherein Quercetin is administered intravenously, wherein the dose of Quercetin in a solution for intravenous administration is about 0.05 g to about 10 g, and wherein cyclophosphamide is administered intravenously, wherein the cyclophosphamide is in a solution for intravenous administration.

In some embodiments, the combinations in the compositions, and the compositions for the kits, uses and/or methods described herein comprise, consist of, or consist essentially of, Quercetin+cyclophosphamide, wherein Quercetin is administered orally, wherein the amount of Quercetin in a composition for oral administration is about 100 mg to about 50 g, and wherein cyclophosphamide is administered orally, wherein the cyclophosphamide is in a composition for oral administration.

In some embodiments, the combinations in the compositions, and the compositions for the kits, uses and/or methods described herein comprise, consist of, or consist essentially of, Quercetin+cyclophosphamide, wherein Quercetin is administered in a liposomal formulation, wherein the dose of Quercetin for administration in a liposomal formulation is about 25 mg a day to about 100 mg a day, and wherein cyclophosphamide is either administered intravenously, wherein the cyclophosphamide is in a solution for intravenous administration, or wherein cyclophosphamide is administered orally, wherein the cyclophosphamide is in a composition for oral administration.

In some embodiments, the combinations in the compositions, and the compositions for the kits, uses and/or methods described herein comprise, consist of, or consist essentially of, SPB+cyclophosphamide, wherein SPB is administered intravenously, wherein the concentration of SPB in a solution for intravenous administration is about 20 mg/ml to about 2000 mg/ml, and wherein cyclophosphamide is administered intravenously, wherein the cyclophosphamide is in a solution for intravenous administration.

In some embodiments, the combinations in the compositions, and the compositions for the kits, uses and/or methods described herein comprise, consist of, or consist essentially of, SPB+cyclophosphamide, wherein SPB is administered intravenously, wherein the dose of SPB in a solution for intravenous administration is about 0.5 g to about 100 g, and wherein cyclophosphamide is administered intravenously, wherein the cyclophosphamide is in a solution for intravenous administration.

In some embodiments, the combinations in the compositions, and the compositions for the kits, uses and/or methods described herein comprise, consist of, or consist essentially of, SPB+cyclophosphamide, wherein SPB is administered orally, wherein the amount of SPB in a composition for oral administration is about 0.1 g to about 50 g, and wherein cyclophosphamide is administered orally, wherein the cyclophosphamide is in a composition for oral administration.

In some embodiments, the combinations in the compositions, and the compositions for the kits, uses and/or methods described herein comprise, consist of, or consist essentially of, EGCG+cyclophosphamide, wherein EGCG is administered intravenously, wherein the concentration of EGCG in a solution for intravenous administration is about 5 mg/ml to about 100 mg/ml, and wherein cyclophosphamide is administered intravenously, wherein the cyclophosphamide is in a solution for intravenous administration.

In some embodiments, the combinations in the compositions, and the compositions for the kits, uses and/or methods described herein comprise, consist of, or consist essentially of, EGCG+cyclophosphamide, wherein EGCG is administered intravenously, wherein the dose of EGCG in a solution for intravenous administration is at a dose of about 0.01 g to about 15 g, and wherein cyclophosphamide is administered intravenously, wherein the cyclophosphamide is in a solution for intravenous administration.

In some embodiments, the combinations in the compositions, and the compositions for the kits, uses and/or methods described herein comprise, consist of, or consist essentially of, EGCG+cyclophosphamide, wherein EGCG is administered orally, wherein the amount of EGCG in a composition for oral administration is about 0.1 g to about 3 g, and wherein cyclophosphamide is administered orally, wherein the cyclophosphamide is in a composition for oral administration.

In some embodiments, the combinations in the compositions, and the compositions for the kits, uses and/or methods described herein comprise, consist of, or consist essentially of, Quercetin+SPB+cyclophosphamide. In some embodiments, the combinations in the compositions, and the compositions for the kits, uses and/or methods described herein comprise, consist of, or consist essentially of, Quercetin+EGCG+cyclophosphamide. In some embodiments, the combinations in the compositions, and the compositions for the kits, uses and/or methods described herein comprise, consist of, or consist essentially of, SPB+EGCG+cyclophosphamide. In some embodiments, the combinations in the compositions, and the compositions for the kits, uses and/or methods described herein comprise, consist of, or consist essentially of, Quercetin+SPB+EGCG+cyclophosphamide.

The formulations of compositions and compositions for the kits, uses and/or methods described herein include but are not limited to the combinations provided in Table 3 below.

TABLE 3

Combinations for formulations of compositions and compositions for the kits, uses and/or methods described herein

| Combination | Cyclo-phosphamide; Oral | Cyclo-phosphamide; IV | Quercetin IV; about 5 mg/ml to about 500 mg/ml | Quercetin IV; about 0.05 g to about 10 g | Quercetin Oral; about 100 mg to about 50 g | Quercetin Liposomal; about 25 mg a day to about 100 mg a day | SPB IV; about 20 mg/ml to about 2000 mg/ml | SPB IV; about 0.5 g to about 100 g | SPB Oral; about 0.1 g to about 50 g | EGCG IV: about 5 mg/ml to about 100 mg/ml | EGCG IV; about 0.01 g to about 15 g | EGCG Oral; about 0.1 g to about 3 g |
|---|---|---|---|---|---|---|---|---|---|---|---|---|
| 1. | X | | | | X | | | | | | | |
| 2. | X | | | | | X | | | | | | |
| 3. | X | | | | | | | | X | | | |
| 4. | X | | | | | | | | | | | X |
| 5. | X | | | | X | | | | X | | | |
| 6. | X | | | | X | | | | | | | X |
| 7. | X | | | | | | | | X | | | X |
| 8. | X | | | | X | | | | X | | | X |
| 9. | X | | | | | X | | | X | | | |
| 10. | X | | | | | X | | | | | | X |

TABLE 3-continued

Combinations for formulations of compositions and compositions for the kits, uses and/or methods described herein

| Combination | Cyclo-phosphamide; Oral | Cyclo-phosphamide; IV | Quercetin IV; about 5 mg/ml to about 500 mg/ml | Quercetin IV; about 0.05 g to about 10 g | Quercetin Oral; about 100 mg to about 50 g | Quercetin Liposomal; about 25 mg a day to about 100 mg a day | SPB IV; about 20 mg/ml to about 2000 mg/ml | SPB IV; about 0.5 g to about 100 g | SPB Oral; about 0.1 g to about 50 g | EGCG IV; about 5 mg/ml to about 100 mg/ml | EGCG IV; about 0.01 g to about 15 g | EGCG Oral; about 0.1 g to about 3 g |
|---|---|---|---|---|---|---|---|---|---|---|---|---|
| 11. | X | | | | | X | | | X | | | X |
| 12. | X | | X | | | | | | | | | |
| 13. | X | | | X | | | | | | | | |
| 14. | X | | | | | X | | | | | | |
| 15. | X | | | | | | X | | | | | |
| 16. | X | | | | | | | X | | | | |
| 17. | X | | | | | | | | | X | | |
| 18. | X | | | | | | | | | | X | |
| 19. | X | | X | | | | X | | | | | |
| 20. | X | | X | | | | | | | X | | |
| 21. | X | | | | | | X | | | X | | |
| 22. | X | | | X | | | | X | | | | |
| 23. | X | | | X | | | | | | | X | |
| 24. | X | | | | | | | X | | | X | |
| 25. | X | | | | X | | X | | | | | |
| 26. | X | | | | X | | | | | X | | |
| 27. | X | | | | X | | | X | | | | |
| 28. | X | | | | X | | | | | | X | |
| 29. | X | | | | | X | X | | | | | |
| 30. | X | | | | | X | | | | X | | |
| 31. | X | | | | | X | | X | | | | |
| 32. | X | | | | | X | | | | | X | |
| 33. | X | | X | | | | X | | | X | | |
| 34. | X | | X | | | | X | | | | X | |
| 35. | X | | X | | | | | X | | X | | |
| 36. | X | | X | | | | | X | | | X | |
| 37. | X | | | | X | | X | | | X | | |
| 38. | X | | | | X | | X | | | | X | |
| 39. | X | | | | X | | | X | | X | | |
| 40. | X | | | | X | | | X | | | X | |
| 41. | | X | | | X | | | | | | | |
| 42. | | X | | | | X | | | | | | |
| 43. | | X | | | | | | | X | | | |
| 44. | | X | | | | | | | | | | X |
| 45. | | X | | | X | | | | X | | | |
| 46. | | X | | | | X | | | | | | |
| 47. | | X | | | | | | | X | | | X |
| 48. | | X | | | X | | | | X | | | X |
| 49. | | X | | | | X | | | X | | | |
| 50. | | X | | | | X | | | | | | X |
| 51. | | X | | | | X | | | X | | | X |
| 52. | | X | X | | | | | | | | | |
| 53. | | X | | X | | | | | | | | |
| 54. | | X | | | | X | | | | | | |
| 55. | | X | | | | | X | | | | | |
| 56. | | X | | | | | | X | | | | |
| 57. | | X | | | | | | | | X | | |
| 58. | | X | | | | | | | | | X | |
| 59. | | X | X | | | | X | | | | | |
| 60. | | X | X | | | | | | | X | | |
| 61. | | X | | | | | X | | | X | | |
| 62. | | X | | X | | | | X | | | | |
| 63. | | X | | X | | | | | | | X | |
| 64. | | X | | | | | | X | | | X | |
| 65. | | X | | | X | | X | | | | | |
| 66. | | X | | | X | | | | | X | | |
| 67. | | X | | | X | | | X | | | | |
| 68. | | X | | | X | | | | | | X | |
| 69. | | X | | | | X | X | | | | | |
| 70. | | X | | | | X | | | | X | | |
| 71. | | X | | | | X | | X | | | | |
| 72. | | X | | | | X | | | | | X | |
| 73. | | X | X | | | | X | | | X | | |
| 74. | | X | X | | | | X | | | | X | |
| 75. | | X | X | | | | | X | | X | | |

TABLE 3-continued

Combinations for formulations of compositions and compositions for the kits, uses and/or methods described herein

| Combination | Cyclo-phosphamide; Oral | Cyclo-phosphamide; IV | Quercetin IV; about 5 mg/ml to about 500 mg/ml | Quercetin IV; about 0.05 g to about 10 g | Quercetin Oral; about 100 mg to about 50 g | Quercetin Liposomal; about 25 mg a day to about 100 mg a day | SPB IV; about 20 mg/ml to about 2000 mg/ml | SPB IV; about 0.5 g to about 100 g | SPB Oral; about 0.1 g to about 50 g | EGCG IV; about 5 mg/ml to about 100 mg/ml | EGCG IV; about 0.01 g to about 15 g | EGCG Oral; about 0.1 g to about 3 g |
|---|---|---|---|---|---|---|---|---|---|---|---|---|
| 76. | | X | X | | | | | X | | | X | |
| 77. | | X | | X | | | X | | X | | | |
| 78. | | X | | X | | | X | | | | X | |
| 79. | | X | | X | | | | X | X | | | |
| 80. | | X | | X | | | | X | | | X | |

In Table 3, "X" indicates the components of the combinations for formulations of compositions and compositions for the kits, uses and/or methods described herein. Intravenous dosing of cyclophosphamide can be, but is not limited to, 40 mg/kg to 50 mg/kg in divided doses over a period of 2 to 5 days, or 10 mg/kg to 15 mg/kg every 7 to 10 days, or 3 mg/kg to 5 mg/kg twice weekly. Oral dosing cyclophosphamide can be, but is not limited to, 1 mg per kg per day to 5 mg per kg per day, or 1 mg/kg/day to 5 mg/kg/day, or 2 mg/kg/day for 8 to 12 weeks (maximum cumulative dose 168 mg per kg). In some embodiments, including those in Table 3, in a combination comprising Quercetin and SPB, the ratio of the concentration and/or dosing of Quercetin and SPB ranges from about 1:2 to about 1:30. In some embodiments, including those in Table 3, in a combination comprising Quercetin and SPB, the ratio of the concentration and/or dosing of Quercetin and SPB is about 1:10. In some embodiments, including those in Table 3, in a combination comprising Quercetin and SPB, the ratio of the concentration and/or dosing of Quercetin and SPB is about 1:1.25, 1:1.5, 1:1.75, 1:2, 1:4, 1:6, 1:8, 1:10, 1:12, 1:14, 1:16, 1:18, 1:20, 1:22, 1:24, 1:26, 1:28, 1:30, 1:32, 1:34, 1:36, 1:38, 1:40, or a ratio within a range defined by any two of the aforementioned ratios.

In some embodiments, including but not limited to those in Table 3, the dose of Quercetin ranges from about 0.5 g to about 2 g. In some embodiments, the dose of quercetin is about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5 or 10 g, or within a range defined by any two of the aforementioned values. In some embodiments, the dose of SPB ranges from about 1 g to 15 g. In some embodiments, SPB is administered orally at a dose of about 0.2, 0.3, 0.4, 0.5, 0.6, 0.7, 0.8, 0.9, 1, 1.5, 2, 2.5 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, or 75 g, or within a range defined by any two of the aforementioned values.

EXAMPLES

The following Examples are non-limiting. The cells lines, concentrations and doses of the anti-cancer agents and modulators disclosed in the following Examples are non-limiting. Other acceptable concentrations, ranges of concentrations, doses or ranges of doses are also contemplated.

Example 1—Cell Lines and Maintenance, Preparation of Modulators, MiCK® Assay and Data Analysis Non-limiting examples of cells used included AU-565 (breast carcinoma), MCF-7 (breast adenocarcinoma); MDA-MB-468 (breast adenocarcinoma), NCI-H23 (lung adenocarcinoma), NCI-H460 (non-small cell lung carcinoma), NCI-H1299 (non-small cell lung carcinoma), BxPC-3 (pancreatic adenocarcinoma), MIA PaCa-2 (pancreatic adenocarcinoma), Malme-3M (malignant melanoma), A-172 (glioblastoma), MES-SA (uterine sarcoma). These cell lines were already resistant to one or more anti-cancer agents.

The cells lines were grown and maintained in their specific cell culture medium without phenol red, supplemented with 10% FBS, 100 U/mL penicillin and 100 µg/mL streptomycin in humidified air with 5% $CO_2$ at 37° C. Before use, exponentially growing cells were harvested, washed with pre-warmed medium and then re-suspended in complete medium.

A stock solution of quercetin was prepared in 20% DMSO at a concentration of 500 µM and then diluted to 100 µM in the culture medium. The final concentration of DMSO in the well was 1% or less. A slight yellow color was encountered but the color was not considered significant in the assay. Sodium phenyl butyrate was dissolved in RPMI at a concentration of 20 µM without an interfering color development. Epigallocatechin-3-gallate was dissolved in RPMI at a concentration of 10 µg/mL.

The MicroCulture® Kinetic (MiCK®) assay was used to detect and quantitate apoptotic cell death in a population of cells. The cells of interest are exposed to the drug(s) of interest in the wells of a 384 well spectrophotometric plate with RPMI or DMEM as a support medium. Changes in cell shape are detected by automated spectrophotometric readings automatically recorded every five minutes.

The optical density (OD) readings obtained in the MiCK® assay were plotted versus time to obtain a curve. The slope of the obtained curve was used in a proprietary equation to determine the amount of apoptosis induced. The unit of measure was the kinetic unit (KU). Although the disclosure refers to tests occurring in the wells of a 384 well spectrophotometric plate, one of skill in the art will recognize that numerous test sites are suitable for the test disclosed herein, and therefore, a 384 well spectrophotometric plate is a not limiting embodiment. For example, spectrophotometric plates of other sizes (6, 12, 24, 48, 96 well plates), cuvettes, test tubes, or any other suitable structure known in the art can be used.

Example 2—Results with Cyclophosphamide for BxPC-3, MIA-PaCa 2, and MCF-7 Cell Lines Using the methods provided in Example 1, the effect of the combination of cyclophosphamide with quercetin (S1) and SPB (S2) was tested on BxPC-3, MIA-PaCa 2, and MCF-7 cell lines. For the pancreatic adenocarcinoma cell line BxPC-3, the combination of cyclophosphamide and S1+S2 produced a synergistic effect as compared to cyclophosphamide alone or the combination of S1+S2 alone. The concentration of cyclophosphamide used was 200 M, the concentration of S1 used was 100 μM, and the concentration of S2 used was 20 μM. The combination of cyclophosphamide and S1+S2 produced an increase in KU values of about 3 fold. Results of the MiCK® assay for the BxPC-3 cell line are shown in FIG. 1.

For the pancreatic adenocarcinoma cell line MIA-PaCa 2, the combination of cyclophosphamide and S1+S2 produced a synergistic effect as compared to cyclophosphamide alone or the combination of S1+S2 alone. The concentration of cyclophosphamide used was 200 μM, the concentration of S1 used was 100 μM, and the concentration of S2 used was 20 μM. The combination of cyclophosphamide and S1+S2 produced an increase in KU values of about 30 fold. Results of the MiCK® assay for the MIA-PaCa 2 cell line are shown in FIG. 2.

Figure 3:
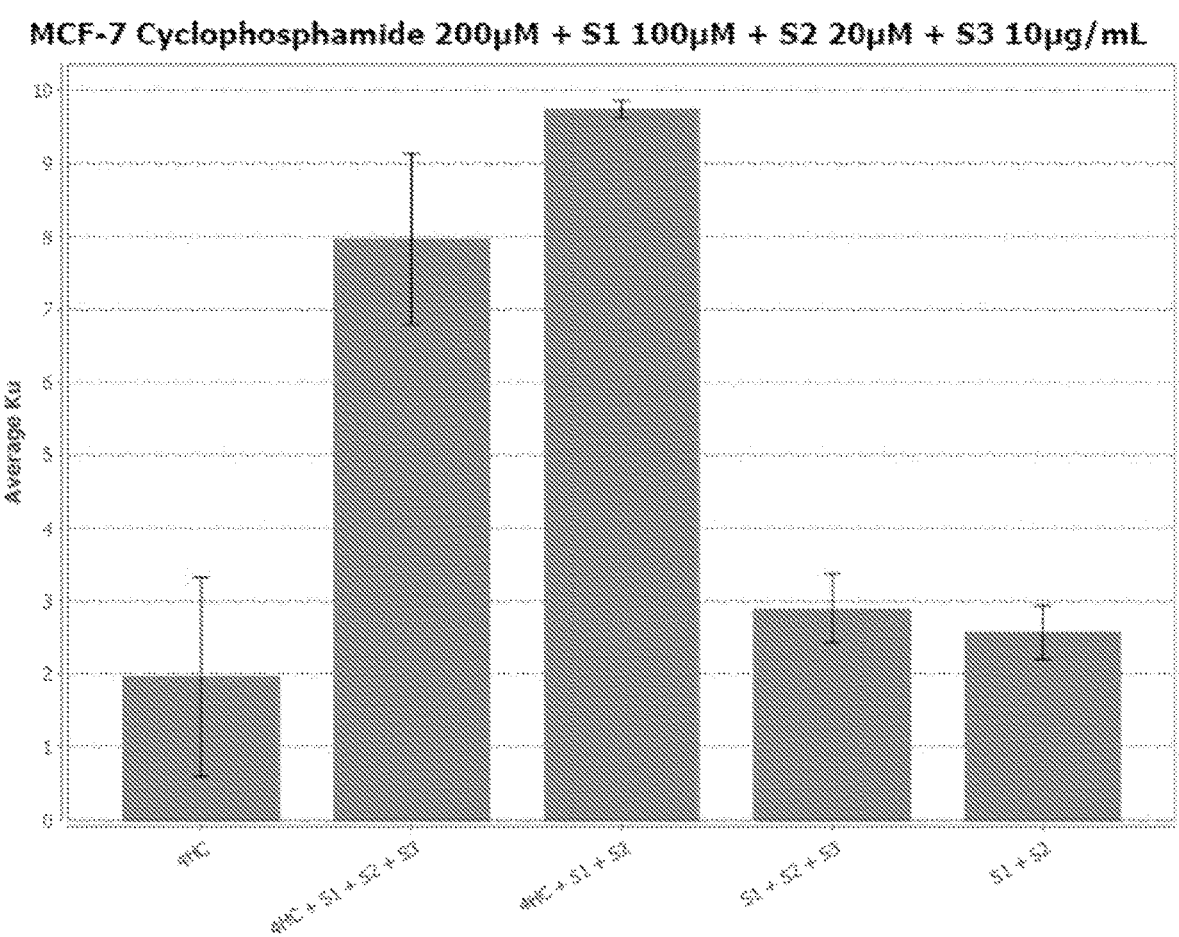
FIG. 3 shows a bar graph of the effect of cyclophosphamide alone, cyclophosphamide with S1+S2, and cyclophosphamide with S1+S2+S3 on MCF-7 cell line. Also shown are the effects of S1+S2, and S1+S2+S3 without cyclophosphamide. Standard deviations are shown. All results are report in kinetic unit (KU).

For the pancreatic adenocarcinoma cell line MCF-7, the combination of cyclophosphamide and S1+S2 produced a synergistic effect as compared to cyclophosphamide alone or the combination of S1+S2 alone. The concentration of cyclophosphamide used was 200 μM, the concentration of S1 used was 100 μM, and the concentration of S2 used was 20 μM. The combination of cyclophosphamide and S1+S2 produced an increase in KU values of about 3 fold. Results of the MiCK® assay for the MCF-7 cell line are shown in FIG. 3.

These results were particularly surprising given that cyclophosphamide is a pro-drug, which is converted into its active form following metabolism in the liver, cyclophosphamide is not believed to be metabolized in vitro and not expected to have an effect in vitro. Nevertheless, a synergistic effect was observed with cyclophosphamide and S1+S2 as compared to cyclophosphamide alone or the combination of S1+S2 alone.

Example 3

One or more patients are identified who have one or more cancers selected from lung carcinoma, prostate cancer, glioblastoma multiform, hormone refractory prostate cancer, solid tumor malignancies such as colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, and bladder cancer.

The one or more patients are administered a formulation comprising cyclophosphamide only. Cyclophosphamide is given at various doses including intravenous 40 mg/kg to 50 mg/kg in divided doses over a period of 2 to 5 days, intravenous 10 mg/kg to 15 mg/kg every 7 to 10 days, or intravenously 3 mg/kg to 5 mg/kg twice weekly. Oral cyclophosphamide is administered at 1 mg/kg/day to 5 mg/kg/day, or 2 mg/kg/day for 8 to 12 weeks for a maximum cumulative dose 168 mg/kg. On the day of the next administration and prior to the administration, as assessment of the outcome of treatment until that point is conducted and compared to all previous assessments.

Assessment of the patients after an initial period of treatment in terms of parameters such as cancer progression, growth and size, indicates that the cancers have not progressed, slowed in growth, stopped growing/progressing, reduced in size, and/or eliminated. However, following the initial response period, patients show a decline in response to 4HC. The cancers eventually become resistant to 4HC. The cancers resume progressing and growing in size.

Patients are then administered a combination of cyclophosphamide and quercetin and SPB. Oral cyclophosphamide is given at doses of about 50 mg per day to about 150 mg per day to an "on" and "off" schedule of 1-14 days "on" and 14-28 days "off" in 28 day schedule, as a metronomic dose. Standard dose of cyclophosphamide for oral administration for initial and maintenance dose in leukemias is about 1 mg/kg to about 5 mg/kg. Intravenous dose of cyclophosphamide include about 40 mg/kg to about 50 mg/kg (total course dose) in divided doses given over 2 to 5 days. Other IV regimens include cyclophosphamide at about 10 mg/kg to about 15 mg/kg every 7 to 10 days or cyclophosphamide at about 3 mg/kg to about 5 mg/kg twice weekly. Routinely, cyclophosphamide is used IV at about 440 mg/m2 to about 600 mg/m2, up to about 4 g/m2 (about 10 mg/kg to about 15 mg/kg), and orally at about 50 mg to about 150 mg (average 100 mg/m2). An assessment of the outcome of treatment is periodically made.

After a minimum period of treatment (e.g., one day), the patient shows improvement. Assessments of the cancer in terms of parameters such as its progression, growth and/or size, indicates that the cancer has not progressed, slowed in growth, stopped growing/progressing, remained the same or reduced in size, and/or been eliminated. Additional assessment shows that after therapy, patients have improved in one or more measures selected from the group of: Natural Killer cell activity, increased WBC count, decreased LDH activity, decreased tumor markers, shrinkage of tumor in radiographic studies, decrease in CRP (correlation with improved survival), improved IgF-1. In some cases, the patients do not show a decline in response to the combination of cyclophosphamide+quercetin+SPB during the course of the treatment, and the cancers are eventually eliminated without relapse.

Example 4

One or more patients are identified who have one or more cancers selected from lung carcinoma, prostate cancer, glioblastoma multiform, hormone refractory prostate cancer, solid tumor malignancies such as colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, and bladder cancer.

Patients are then administered a combination of cyclophosphamide and quercetin and SPB. Oral cyclophosphamide is given at doses of about 50 mg per day to about 150 mg per day to an "on" and "off" schedule of 1-14 days "on" and 14-28 days "off" in 28 day schedule, as a metronomic dose. Standard dose of cyclophosphamide for oral administration for initial and maintenance dose in leukemias is about 1 mg/kg to about 5 mg/kg. Intravenous dose of cyclophosphamide include about 40 mg/kg to about 50 mg/kg (total course dose) in divided doses given over 2 to 5 days. Other IV regimens include cyclophosphamide at about 10 mg/kg to about 15 mg/kg every 7 to 10 days or cyclophosphamide at about 3 mg/kg to about 5 mg/kg twice weekly. Routinely, cyclophosphamide is used IV at about 440 mg/m2 to about 600 mg/m2, up to about 4 g/m2 (about 10 mg/kg to about 15 mg/kg), and orally at about 50 mg to about 150 mg (average 100 mg/m2). An assessment of the outcome of treatment is periodically made.

After a minimum period of treatment (e.g., one day), the patient shows improvement. Assessments of the cancer in terms of parameters such as its progression, growth and/or size, indicates that the cancer has not progressed, slowed in growth, stopped growing/progressing, remained the same or reduced in size, and/or been eliminated. Additional assessment shows that after therapy, patients have improved in one or more measures selected from the group of: Natural Killer cell activity, increased WBC count, decreased LDH activity, decreased tumor markers, shrinkage of tumor in radiographic studies, decrease in CRP (correlation with improved survival), improved IgF-1. In some cases, the patients do not show a decline in response to the combination of cyclophosphamide+quercetin+SPB during the course of the treatment, and the cancers are eventually eliminated without relapse.

Example 5—Case Study 1

The patient was a 42 years old female with history of serious ovarian adenocarcinoma diagnosed post hysterectomy and oophorectomy. At the time of surgery she was found to have peritoneal carcinomatosis and omental involvement. She was also positive for BRCA2 germ line mutation. She received standard chemotherapy consisting of Taxol and Carboplatinum starting right after the resections and finished treatment four months later (2 cycles of Carbiplatinum every three weeks and weekly taxol). She also received biweekly Avastin starting one month after resections, changed to q 21 day schedule which was scheduled to be continued for 15 months. She has regular follow up assessments. The patient's tumor marker started to rise seven months after initiation of Avastin treatment, at which point in time she was diagnosed with platinum resistance cancer.

The patient was then referred to the clinic of Dr. Nezami for further treatment. On first analysis, 10 months after the resections, she was symptomatic with nausea and vomiting. Her laboratory test results indicated increased insulin like growth factor one (IGF-1) at 302 ng/ml and elevated CA 125 levels. She was immediately started on IV therapies using compositions comprising a combination of cyclophosphamide, quercetin alone or with SPB on daily basis four times a week. The cyclophosphamide was administered orally at 50 mg per day, the quercetin was administered intravenously at 1 g per treatment session, and the SPB was administered at 4 g IV. The patient rapidly responded to the treatments. The patient's IGF-1 dropped from 302 ng/ml to 227 ng/ml after receiving three treatments. Her CA 125 dropped slightly at 40.6 U/ml and her vomiting stopped. After 16 treatments, (received over 4 weeks, 4 days a week, her treatment was reduced to a biweekly treatment, during which she received treatment twice a week every other week. Her IGF-1 dropped further to 27 ng/ml about 16 weeks after initiation of treatment (from 302 ng/ml) receiving treatments on a biweekly program. Imaging (CT chest/abdomen and pelvis) conducted about 6 months after starting treatment revealed that she had no evidence of metastatic disease. In summary, there was significant improvement in her laboratory and imaging findings after receiving the combinational therapy with cyclophosphamide, quercetin and SPB.

Example 6—Case Study 2

A 53 year old female with history of poorly differentiated left breast adenocarcinoma as confirmed by biopsy and with no conventional post-diagnosis treatment referred to the clinic of Dr. Nezami for assessment and treatments. She had a germline mutated BRCA 1 gene. On arrival she was asymptomatic except that she had a palpable oval mass at 12 o'clock in the left breast sized about 4 cm to 5 cm with fibrocystic changes in other areas as well as right breast. The patient refused all conventional therapies. A prior scan before initiation of treatment with a combination of cyclophosphamide, quercetin with and without SPB had revealed two masses in left breast. Both were biopsied and both showed infiltrating poorly differentiated (Nottingham grade 3) ductal carcinoma with ductal carcinoma in situ (DCIS). The patient was immediately started treatment with cyclophosphamide in conjunction with quercetin & SPB. The cyclophosphamide was administered orally at 50 mg per day, the quercetin was administered at 500 mg to 1.5 g per day and the SPB was administered at 4 g to 6 g per session IV on a daily basis.

Upon completing a round of ten treatments (received over 2 weeks, 5 days a week), the patient was re-evaluated. The patient's quality of life had improved as measured by ECOG performance status. The patient showed improved function and memory. On examination she was found to have no palpable mass in the left breast after six treatments. Her tumor markers were normal. Her CT scan was repeated after 25 days and revealed no sign of tumor in the left breast at the site of biopsy. Only one of the two biopsy proven malignancies was evident in the left breast. The size was 1.9×1.2×1.7 cm in MRI and 1.3 cm in the high resolution CT scan of the breast, which had decreased from 4×2 cm measured just before starting the initiation of treatment. No distant or local sites of invasion were identified.

Follow up laboratory assessments about 15 weeks after initiation of treatment confirmed stable tumor markers (Cancer Antigen (CA) 15-3 at 15.6 U/ml down from 17.6 U/ml, normal LDH at 123 IU/L (down from 179 IU/L) Her examination revealed no tumor. Her CA 15-3 dropped even further to 9.4 IU/L as measured 12 weeks later.

The patient left California and did not receive any further treatment with cyclophosphamide, quercetin and SPB for a year. She then returned after exhausting many alternative modalities in Mexico as well as hormonal therapies. Her tumor had grown substantially from 1.9 cm to 3.6 cm, which was confirmed by ultrasounds. Upon her return 15 months later, a restaging PET imaging and laboratory assessments confirmed the progression of disease despite hormonal therapies. The patient was started on treatments using the cyclophosphamide, quercetin and SPB, which she received for 12 weeks on twice weekly schedule. The cyclophosphamide was administered at 50 mg daily orally, the quercetin was administered 500 mg to 1.5 g IV, and the SPB was administered at 4 g to 6 g IV daily.

Restaging PET scan about 8 weeks after re-initiation of treatment confirmed stable disease per activity with no statistical change. On scan, the size of the tumor had increased slightly from 3.9 cm to 4.4 cm, although the velocity of growth was decreased. No new lesions were identified in her scan and her staging remained stable. She was scheduled for mastectomy, and further maintenance treatments once a week and further scans every three months.

The patient consented to modified-radical mastectomy with lymph node dissection (performed about 12 weeks after re-initiation of treatment) but refused radiation and chemotherapies. Her pathology about 13 weeks after re-initiation of treatment revealed invasive ductal carcinoma (3.8 cm; grade III) with one positive lymph node (1/12). An Oncotype DX Test was performed on the tumor, which showed a recurrence score of 50 percent, suggestive of requirement of chemotherapy, which was refused by the patient. Patient continued her therapy on compositions comprising cyclophosphamide, quercetin and SPB on a weekly basis. A restaging PET scan performed four months later revealed no residual disease with normal uptake after six months of remission. She continued treatment at maintenance level for one year, during which cyclophosphamide was administered at 50 mg orally per day, the quercetin was administered 500 mg to 1.5 g IV, and the SPB was administered 4 g to 6 g IV before discontinuing treatment.

Twenty-two months after her restaging PET scan, the patient had developed increased tumor marker CA 125. An ultrasound and PET scan suspected bilateral masses in the ovaries that were resected by bilateral oophorectomy, which proved to be high grade bilateral papillary serous malignant adenocarcinoma with positive somatic BRCA1 mutations as well as ERBB4, NF-1, PDGFR and MSH6 mutations. Further treatment with cyclophosphamide, quercetin and SPB was provided, during which time cyclophosphamide was administered at 50 mg orally per day, the quercetin was administered 500 mg to 1.5 grams IV, and the SPB was administered 4 g to 6 g IV, on a twice per week basis in average, tapered down to once a week treatment, and currently on once a month treatment, as maintenance, still remains in remission.

In summary, this case is related to the disappearance of a biopsy-proven breast malignancy following treatment with a combination of cyclophosphamide, quercetin and SPB. The patient did not experience any negative side effects. The treatment was able to stabilize cancer growth despite having failed hormonal therapies. To our knowledge this is the first reported case of excellent remissions of breast and bilateral ovarian cancers without administration any conventional chemotherapy regimens. To our knowledge no comparable therapy has been as effective in treating BRCA positive germline and somatic breast and ovarian cancer in single patient. Remarkably, the patient remains in remission after three years without any infusional chemotherapy or radiation.

Example 7—Case Study 3

This is a case study of a 62 year old female with history of left ductal breast carcinoma diagnosed after biopsy. The patient further received cryoablation of her breast mass. The tumor was initially found to have a high recurrence score of 33 by oncotype dx, and was ER positive/PR and HER2 negative. The patient was referred to the clinic of Dr. Nezami after exhausting several different alternative therapies with unknown results, including GC Maf, Salicinium and conventional therapies (including hormonal blockade with letrozole). She was asymptomatic, except for burning sensation at her cryoablated left breast.

Upon her arrival at the clinic of Dr. Nezami, she was evaluated by her laboratory test results, and her tumor molecular profiling was obtained. Her laboratory tests showed that her plasma vascular endothelial growth factor (VEGF) was elevated at 120.

At the start of her treatment, molecular profiling of circulating tumor cells (CTCs) was performed as follows. In order to obtain CTCs from the patient's peripheral blood, large cells and cell-clusters as well as epithelial cells were isolated. A preparation of mononuclear cells (MNC) served as a control cell fraction. mRNA was ioslated from all fractions. Thereafter, the expression of tumor relevant genes was measured by quantitative real-time RT-PCR. A preparation of mononuclear cells (MNC) served as a control cell fraction.

The expression of the telomerase gene can be increaed in most tumor types but not in normal tissue. An increased expression of telomerase gene may be indicative of the presence of tumor cells in the circulation. Expression of telomerase was elevated in the isoalted cells. Overexpression of C-MYC indicates an increased proliferation of the ioslated cells, and an increased proliferation rate is a typical feature of tumor cells. The expression level of C-MYC in her sample was elevated. Overexpression of ERBB2 (HER2/NEU) is a trait of different types of cancer and may also be observed in breast cancer. Thus, the detection of ERBB2 overexpression may be indicative of the preence of ciruclaitng tumor cells. The expression of ERBB2 in her sample was elevated. The detection of expression of cytokeratin (CK) 19 indicates the presence of epithelial cells and may thus be indicative for circulating tumor cells. There was no expression of CK19 detected in the sample. Thus, in the isolated tumor cell fraction, expression of ERBB2, C-MYC, and telomerase was above threshold (>2.0), i.e., ERBB2 was at 4.36, C-MYC was at 3.98, and telomerase was at 5.77. This finding was indicative of the likely presence of circulating tumor cells in the analyzed blood sample. Thus, her laboratory results showed presence of CTCs in the blood along with expression of ERBB2, C-MYC, and telomerase. The CTCs were ER negative. This is in contrast to the initial findings that showed that the tumor was ER positive/PR and HER2 negative.

A Guardant360 Tumor Response Map illustrates the relative changes of observed cell-free DNA (cfDNA) at different sample submission time points. The "Somatic Alteration Burden" value refers to the maximum % cfDNA detected at each time point. Amplifications are not plotted, and only the first and last four test dates are plotted. The percentage, or allele frequency, of altered % cfDNA circulating in blood is related to the unique tumor biology of each patient. Factors that may affect the % cfDNA of detected somatic alterations include tumor growth, turn-over, size, heterogeneity, vascularization, disease progression, and treatment. The genes covered by the Guardant360 Tumor Response Map are listed in Table 4.

TABLE 4

Genes detected by Guardant360 Tumor Response Map
Complete Sequencing of Covered Exons*

| Point Mutations (SNVs) (73 Genes) | | | | | | | Indels (23 Genes) | | Amplifications (CNVs) (18 Genes) | | | Fusions (6 Genes) |
|---|---|---|---|---|---|---|---|---|---|---|---|---|
| AKT1 | ALK | APC | AR | ARAF | ARID1A | ATM | ATM | APC | AR | BRAF | | ALK |
| BRAF | BRCA1 | BRCA2 | CCND1 | CCND2 | CCNE1 | CDH1 | ARID1A | BRCA1 | CCND1 | CCND2 | | FGFR2 |
| CDK4 | CDK6 | CDKN2A | CTNNB1 | DDR2 | EGFR | ERBB2 | BRCA2 | CDH1 | CCNE1 | CDK4 | | FGFR3 |
| ESR1 | EZH2 | FBXW7 | FGFR1 | FGFR2 | FGFR3 | GATA3 | CDKN2A | EGFR | CDK6 | EGFR | | NTRK1 |
| GNA11 | GNAQ | GNAS | HNF1A | HRAS | IDH1 | IDH2 | ERBB2 | GATA3 | ERBB2 | FGFR1 | | RET |
| JAK2 | JAK3 | KIT | KRAS | MAP2K1 | MAP2K2 | MAPK1 | KIT | MET | FGFR2 | KIT | | ROS1 |
| MAPK3 | MET | MLH1 | MPL | MTOR | MYC | NF1 | MLH1 | MTOR | KRAS | MET | | |
| NFE2L2 | NOTCH1 | NPM1 | NRAS | NTRK1 | NTRK3 | PDGFRA | NF1 | PDGFRA | MYC | PDGFRA | | |
| PIK3CA | PTEN | PTPN11 | RAF1 | RB1 | RET | RHEB | PTEN | RB1 | PIK3CA | RAF1 | | |
| RHOA | RIT1 | ROS1 | SMAD4 | SMO | STK11 | TERT** | SMAD4 | STK11 | | | | |
| TP53 | TSC1 | VHL | | | | | TP53 | TSC1 | | | | |
| | | | | | | | VHL | | | | | |

*Exons selected to maximize detection of known somatic mutations. List available upon request
**includes TERT promoter region Results of % cfDNA detected are categorized as follows: ND represents genomic alterations not detected. Genomic alterations may be present that are below the limit of detection of this test. Certain sample or variant characteristics may result in reduced analytic sensitivity, such as poor sample quality or improper collection. Genomic alterations in a tumor may be present but are not detected in circulating cell-free DNA from this blood specimen with this test. Similar to other alterations in circulating cfDNA, the amount (% cfDNA) of this variant may reflect disease progression or response to treatment. Therefore, clinical correlation is advised. As the absolute number of copies in circulation is dependent on both tumor fraction and the magnitude of the tumor amplification, amplifications are reported on a semi-quantitative scale; Positive (+) refers to amplification magnitude is in the lower 50$^{th}$ percentile of samples with amplifications; Strongly Positive (++) refers to amplification magnitude is in the 50th to 90th percentile; Very Strongly Positive (+++) refers to amplification magnitude is in the top 10th percentile. Positive (+) refers to amplification magnitude is in the lower 50$^{th}$ percentile of samples with amplifications; Strongly Positive (++) refers to amplification magnitude is in the 50th to 90th percentile; Very Strongly Positive (+++) refers to amplification magnitude is in the top 10th percentile.

The patient's tumor molecular profiling confirmed the presence of ER and AR receptors. Her liquid biopsy assay for % cfDNA by Guardant360 Tumor Response Map was negative, but her CTCs were positive for with three markers (Telomerase, c Myc and CK). These results were obtained prior to administration of IV epigenetic therapies.

She was started on IV epigenetic therapies according to the embodiments disclosed herein consisting of quercetin and sodium phenyl butyrate which she received on daily basis for 2 weeks. She did not change her diet or lifestyle. She also did not take any supplements or change her medications. Her laboratory tests were repeated after about 2 weeks of starting treatment with IV epigenetic therapies.

Laboratory tests indicated that her VEGF had decreased to 138, which further decreased to 84 an additional about 2.5 weeks later. Her CTC assay was also repeated around this time. She had no side effects from the treatment and remained stable.

Thereafter, she was started on oral cyclophosphamide in combination with epigenetic therapies (IV quercetin).

Her CTC assay were again repeated about 18 weeks later, and results showed continued reduction. While C-MYC at 2.09, i.e., still slightly above the threshold of 2.0, there was disappearance of two markers, ERBB2 and telomerase, i.e., C-MYC and ERBB3 levels were below the threshold of 2.0. The expression of CK19 had increased and expression at low level was observed for the first time.

She maintained her treatment program with the combination of oral cyclophosphamide (Cytoxan) and IV quercetin, on a one week a month schedule. She remained in complete remission, both documented through breast imaging (MRI) as well as whole body PET scan at the start of her treatment and about seven months later. All her tumor markers also remained in complete normal range. She continued oral Cytoxan for an additional 6 months, and is at present further continuing her treatments on a monthly basis, with no sign of tumor recurrence.

In summary, this case study illustrates successful treatment with a combination of cyclophosphamide and epigenetic therapies. The patient was able to accomplish complete remission with breast cancer, which otherwise would have required treatment with surgery, chemotherapy, radiation therapy, and/or hormonal blockade with aromatase inhibitor. This patient received none of these standard therapies.

The terminology used in the description presented herein is not intended to be interpreted in any limited or restrictive manner and unless otherwise indicated refers to the ordinary meaning as would be understood by one of ordinary skill in the art in view of the specification. Furthermore, embodiments may comprise, consist of, or consist essentially of, several novel features, no single one of which is solely responsible for its desirable attributes or is believed to be essential to practicing the embodiments herein described. As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein.

Although this disclosure is in the context of certain embodiments and examples, those of ordinary skill in the art will understand that the present disclosure extends beyond the specifically disclosed embodiments to other alternative embodiments and/or uses of the embodiments and obvious modifications and equivalents thereof. In addition, while several variations of the embodiments have been shown and described in detail, other modifications, which are within the scope of this disclosure, will be readily apparent to those of ordinary skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes or embodiments of the disclosure. Thus, it is intended that the scope of the present disclosure herein disclosed should not be limited by the particular disclosed embodiments described above.

What is claimed is:

1. A pharmaceutical composition for treatment of a neoplasm, the pharmaceutical composition comprising:
    synergistically effective amounts of:
        at least one anti-cancer agent, wherein the at least one anti-cancer agent is oral cyclophosphamide, and wherein the amount of cyclophosphamide is about 50 mg to about 150 mg;
        a first anti-cancer response modulator, wherein the first anti-cancer response modulator is intravenous quercetin; and
        a second anti-cancer response modulator, wherein the second anti-cancer response modulator is intravenous sodium phenyl butyrate (SPB).

2. The pharmaceutical composition of claim 1, further comprising a third anti-cancer response modulator wherein the third anti-cancer response modulator is EGCG.

3. The pharmaceutical composition of claim 1, wherein the amount of quercetin is 0.1 g to 2.5 g or the quercetin is in solution at a concentration of 10 mg/ml to 500 mg/ml.

4. The pharmaceutical composition of claim 1, wherein the amount of SPB is 0.1 g to 40 g or the SPB is in solution at a concentration of 50 mg/ml to 500 mg/ml.

5. The pharmaceutical composition of claim 2, wherein the amount of EGCG is 0.1 g to 1.5 g or the EGCG is in solution at a concentration of 5 mg/ml to 500 mg/ml.

6. The pharmaceutical composition of claim 1, wherein the anti-cancer agent and the first and second anti-cancer response modulators are in a single dosage form suitable for either IV or oral co-administration, or the anti-cancer agent and the first and second anti-cancer response modulators are each in separate dosage forms suitable for either IV or oral administration.

7. The pharmaceutical composition of claim 1, wherein the neoplasm is one or more of breast adenocarcinoma, pancreatic adenocarcinoma, lung carcinoma, prostate cancer, glioblastoma multiform, hormone refractory prostate cancer, and a solid tumor malignancy.

8. A kit for treatment of a neoplasm, wherein the kit comprises a pharmaceutical composition comprising:
    synergistically effective amounts of:
        at least one anti-cancer agent, wherein the at least one anti-cancer agent is oral cyclophosphamide, and wherein the amount of cyclophosphamide is about 50 mg to about 150 mg;
        a first anti anti-cancer response modulator, wherein the first anti-cancer response modulator is intravenous quercetin; and
        a second anti anti-cancer response modulator, wherein the second anti-cancer response modulator is intravenous SPB.

9. The kit according to claim 8, wherein each of the at least one anti-cancer agent, the first anti-cancer response modulator, and the second anti-cancer response modulator are contained in a single container each in a single dosage form or the at least one anti-cancer agent, the first anti-cancer response modulator, and the second anti-cancer response modulator are contained in separate sub-containers.

10. A method of treatment of a neoplasm in a patient in need thereof, the method comprising:
    identifying a patient with a neoplasm;
    administering a pharmaceutical composition comprising:
    synergistically effective amounts of:
        at least one anti-cancer agent, wherein the at least one anti-cancer agent is cyclophosphamide, and wherein the cyclophosphamide is administered orally at a dose of about 3 mg/kg to about 50 mg/kg;
        a first anti-cancer response modulator, wherein the first anti-cancer response modulator is intravenous quercetin; and
        a second anti anti-cancer response modulator, wherein the second anti-cancer response modulator is intravenous SPB.

11. The method of claim 10, further comprising a third anti-cancer response modulator wherein the third anti-cancer repose modulator is EGCG.

12. The method of claim 10, wherein the quercetin is administered at a dose of 0.1 g to 2.5 g.

13. The method of claim 10, wherein the SPB is administered at a dose of 0.1 g to 40 g.

14. The method of claim 11, wherein the EGCG is administered at a dose is 0.1 g to 1.5 g.

15. The pharmaceutical composition of claim 7, wherein the solid tumor malignancy is one or more of colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, and bladder cancer.

* * * * *